US012797338B2

(12) United States Patent
Li et al.

(10) Patent No.: US 12,797,338 B2
(45) Date of Patent: Nov. 17, 2026

(54) MODIFIED EXTRACELLULAR VESICLES THAT SPECIFICALLY TARGET KIDNEYS AND METHODS OF PREPARATION AND APPLICATIONS THEREOF

(71) Applicant: ZHONGNAN HOSPITAL OF WUHAN UNIVERSITY, Hubei (CN)

(72) Inventors: Yiming Li, Hubei (CN); Zhiyong Peng, Hubei (CN); Jinmeng Suo, Hubei (CN)

(73) Assignee: ZHONGNAN HOSPITAL OF WUHAN UNIVERSITY, Hubei (CN)

( * ) Notice: Subject to any disclaimer, the term of this patent is extended or adjusted under 35 U.S.C. 154(b) by 470 days.

(21) Appl. No.: 18/527,343

(22) Filed: Dec. 3, 2023

(65) Prior Publication Data

US 2025/0144034 A1 May 8, 2025

(30) Foreign Application Priority Data

Nov. 6, 2023 (CN) ........................ 202311474802.1

(51) Int. Cl.
*A61K 9/50* (2006.01)
*A61K 38/17* (2006.01)
*A61P 13/12* (2006.01)

(52) U.S. Cl.
CPC ........ *A61K 9/5068* (2013.01); *A61K 38/1709* (2013.01); *A61P 13/12* (2018.01)

(58) Field of Classification Search
None
See application file for complete search history.

(56) References Cited

FOREIGN PATENT DOCUMENTS

CN 115212234 10/2022

OTHER PUBLICATIONS

Saleem et al., Stem Cell Research & Therapy (2024) 15:477, 19 pages (Year: 2024).*
Tang et al., JASN 32: 2467-2483, 2021 (Year: 2021).*

* cited by examiner

*Primary Examiner* — Evelyn Y Pyla
(74) *Attorney, Agent, or Firm* — JCIP GLOBAL INC.

(57) ABSTRACT

The present invention discloses a method for the preparation and application of modified extracellular vesicles specifically targeted to the kidneys. These modified extracellular vesicles are derived from fibroblastic reticular cells in the mesentery tissue and express anti-inflammatory proteins after being modified with anchor peptides. By combining the extracellular vesicles secreted from fibroblastic reticular cells in the mesentery tissue with anchor peptides, the present invention ensures the effective targeting of the exosomes to the kidneys. Additionally, through genetic engineering of fibroblastic reticular cells, the exosomes secreted by these cells can carry the target molecule, anti-inflammatory protein CD5L, achieving precise targeted therapy for the kidneys. This innovative treatment strategy holds promising potential for the treatment of sepsis-associated acute kidney injury, bringing positive impacts to patients' health.

1 Claim, 28 Drawing Sheets

Specification includes a Sequence Listing.

| Avg Count | Mean | SD |
|---|---|---|
| 99597 | 61 | 14 |

| Avg Count | Mean | SD |
|---|---|---|
| 162138 | 60 | 14 |

CD63: Red(AF 647) CD81: Green(AF 555) CD9: Blue (AF 488)

LPS+FRC-Exos

LPS

PBS

MODIFIED EXTRACELLULAR VESICLES THAT SPECIFICALLY TARGET KIDNEYS AND METHODS OF PREPARATION AND APPLICATIONS THEREOF

CROSS-REFERENCE TO RELATED APPLICATION

This application claims the priority benefit of Chinese patent application NO. 202311474802.1, filed on Nov. 6, 2023. The entirety of the above-mentioned patent application is hereby incorporated by reference herein and made a part of this specification.

REFERENCE TO A SEQUENCE LISTING

The instant application contains a Sequencing Listing which has been submitted electronically in XML file and is hereby incorporated by reference in its entirety. Said XML copy, created on Dec. 20, 2023, is named 140337US-sequencing_listing and is 5,510 bytes in size.

BACKGROUND

Technical Field

This invention relates to the field of biomedical technology, specifically relating to modified extracellular vesicles that specifically target the kidney and methods of preparation and applications thereof.

Description of Related Art

Sepsis-associated acute kidney injury, as a severe systemic infection complication, involves damage to the kidneys caused by the inflammatory response triggered by the infection. It presents significant challenges in clinical practice and requires a thorough understanding of its pathophysiological mechanisms in order to better address this serious disease. First, the clinical challenges of sepsis-associated acute kidney injury are manifested in several aspects. First, its high incidence rates pose a problem, with over 180,000 cases of severe sepsis leading to acute kidney injury globally each year. Second, the severity of the condition should not be ignored, as statistics show that acute kidney injury is one of the leading causes of mortality in sepsis patients, accounting for up to 50%. Additionally, the early diagnosis of sepsis-associated acute kidney injury is difficult, resulting in patients potentially receiving appropriate treatment when their condition has already deteriorated significantly. Moreover, even with appropriate antibiotic therapy and inflammation suppression strategies, the progression of acute kidney injury cannot always be prevented, making it difficult to control disease progression. Secondly, there is an urgent need for the treatment of sepsis-associated acute kidney injury. Currently, there is a lack of specific treatment methods, with symptomatic support still being the main approach in clinical practice. However, as further research into the pathophysiological mechanisms of sepsis-associated acute kidney injury is conducted, the need for treatment becomes increasingly urgent. For example, intervention in inflammation, alleviation of oxidative stress, and inhibition of cell apoptosis may hopefully in suppressing kidney damage progression. Treatment methods such as anti-inflammatory drugs, antioxidants, and apoptosis inhibitors have shown potential effects in laboratory studies, but further validation of their efficacy and safety is required in clinical applications.

In conclusion, sepsis-associated acute kidney injury is a clinically challenging disease, with its high incidence rates and severe condition resulting in significant health issues. In the absence of specific treatment methods, exploring more effective intervention strategies becomes a top priority. Through a deep understanding of the pathophysiological mechanisms of sepsis-associated acute kidney injury and developing new treatment approaches, it is hoped that better treatment outcomes and prognosis can be achieved for patients.

Extracellular vesicles, as a natural information delivery system, possess unique biological activity that renders them as potential carriers for next-generation therapeutic strategies. However, the application of engineered extracellular vesicles in the treatment of sepsis-associated acute kidney injury still faces several challenges. First, it is necessary to ensure the effective targeting of extracellular vesicles to the kidneys and achieve stable distribution within the body, which poses technical hurdles to overcome. Second, the engineering process of extracellular vesicles requires precise control to ensure consistent and stable drug delivery efficacy.

Therefore, there is an urgent need to develop targeted extracellular vesicle-based therapeutics that can effectively target the kidneys and achieve stable distribution within the body for the treatment and/or prevention of sepsis-associated acute kidney injury.

SUMMARY

The purpose of this invention is to provide a modified extracellular vesicles that specifically target the kidney, and methods of preparation and application thereof. The modified extracellular vesicles can effectively target the kidney and have a stable distribution within the body, as well as stable drug-carrying properties, making them effective for the treatment and/or prevention of sepsis-associated acute kidney injury.

To achieve this goal, the following technical plan is proposed:

In the first aspect of the present invention, a modified extracellular vesicles that specifically target the kidney is provided. This modification is achieved by combining CD5 antigen-like protein expressed on extracellular vesicles secreted by fibroblastic reticular cells from mesentery tissue with an anchoring peptide during incubation.

Furthermore, extracellular vesicles secreted by fibroblastic reticular cells are isolated and extracted by centrifugation, after which their membrane proteins are identified. Positive markers include HSP70, CD81, CD63, and CD9, while negative markers include GM130, Calexin, VDAC1, and TIMM23, all of which come from the mesentery tissue.

Furthermore, the anchor peptide is the KIM-1-targeting peptide.

In the second aspect of the present invention, a method for preparing modified extracellular vesicles (Exos) that specifically target the kidney is provided. The method comprises expressing anti-inflammatory proteins in FRC to obtain loaded anti-inflammatory protein-modified Exos. The loaded Exos are then co-incubated with the anchor peptide or other modified Exos specifically targeting the kidney, hereinafter referred to as anti-inflammatory protein-LTH-FRC-Exos.

In the third aspect of the present invention, the application of the modified Exos that specifically target the kidney in the preparation of drugs for treating and/or preventing sepsis-associated acute kidney injury is provided.

In the fourth aspect of the present invention, a drug for treating and/or preventing sepsis-associated acute kidney injury is provided, comprising at least one of the modified Exos that specifically target the kidney.

In the fifth aspect of the present invention, a method for treating sepsis-associated acute kidney injury in a patient is provided, comprising administering the drug mentioned above. The administration can be done via oral (by mouth), intravenous (IV), intramuscular (IM), intrathecal, subcutaneous (sc), sublingual, buccal, rectal, vaginal, ocular, auricular, nasal (nasal mucosa), inhalation (oral or nasal), topical (skin) or transdermal (systemic via patch on skin) routes, exhibiting local or systemic effects.

One or more technical schemes in the present embodiments of the invention at least have the following technical effects or advantages:

The present invention provides modified extracellular vesicles (EVs) that specifically target to the kidney, and preparation methods and applications thereof. First, through mass spectrometry analysis, the differential expression of CD5L protein in FRC-Exos was found to be the most significant. Furthermore, the expression of CD5L was found to be significantly increased in septic patients. By genetically engineering EVs secreted by fibroblastic reticular cells from the mesentery tissue, the present invention enables the secretion of exosomes carrying the targeted anti-inflammatory molecule CD5L. By combining with anchoring peptides, these exosomes can be effectively targeted to the kidney, achieving precise targeted therapy for renal diseases. The anti-inflammatory protein, LTH-FRC-Exos, derived from this invention, exerts its effects by mediating CD5L anti-inflammatory protein to promote mitochondrial autophagy and inhibit cell apoptosis, thus alleviating kidney damage caused by sepsis. This innovative therapeutic strategy holds the potential to provide new possibilities for the treatment of septic acute kidney injury, positively impacting the health of patients.

BRIEF DESCRIPTION OF THE DRAWINGS

In order to elucidate the technical aspects of the embodiments of the present invention more clearly, a brief introduction to the accompanying figures used in the description of the embodiments will be provided. It is evident that the figures described below represent some embodiments of the present invention, and ordinary technical personnel in the field can obtain additional figures based on them without exerting any creative effort.

FIG. 1A: The morphology of EVs observed under a transmission electron microscope (TEM); scale bars, 500 nm (left) and 100 nm (right).

FIG. 1B: Nano-tracking analysis (NTA) of EVs diameter.

FIG. 1C-IE: Detection of CD81 and CD9 using an automated EVs fluorescence detection analysis system (Nanoview). The chip is spotted with anti-CD81 and anti-CD9, which capture exosomes expressing homologous antibodies. Particle count, diameter, and fluorescence intensity of EVs captured by anti-CD81 and anti-CD9 chips are shown. Scale bars, 10 μm (left and right).

The a-g group of mice underwent CLP surgery, and received intra-peritoneal injection of FRCs (2×105 per mouse) or an equal amount of FRC-derived Exos (300 g per mouse) via tail vein injection one hour later.

Figure 1A:
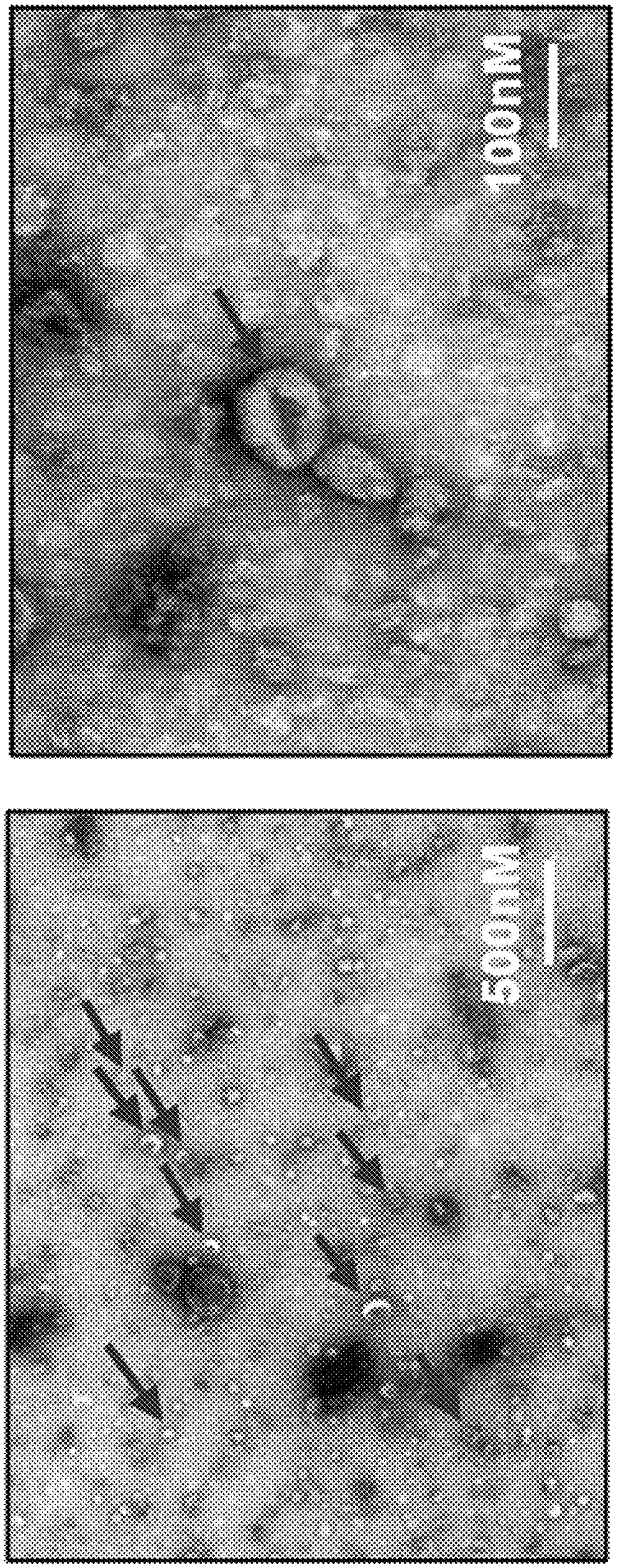
FIG. 1A-1E illustrate the outcomes of FRCs in enhancing renal function and secreting EVs with characteristic Exos features.
Figure 1B:
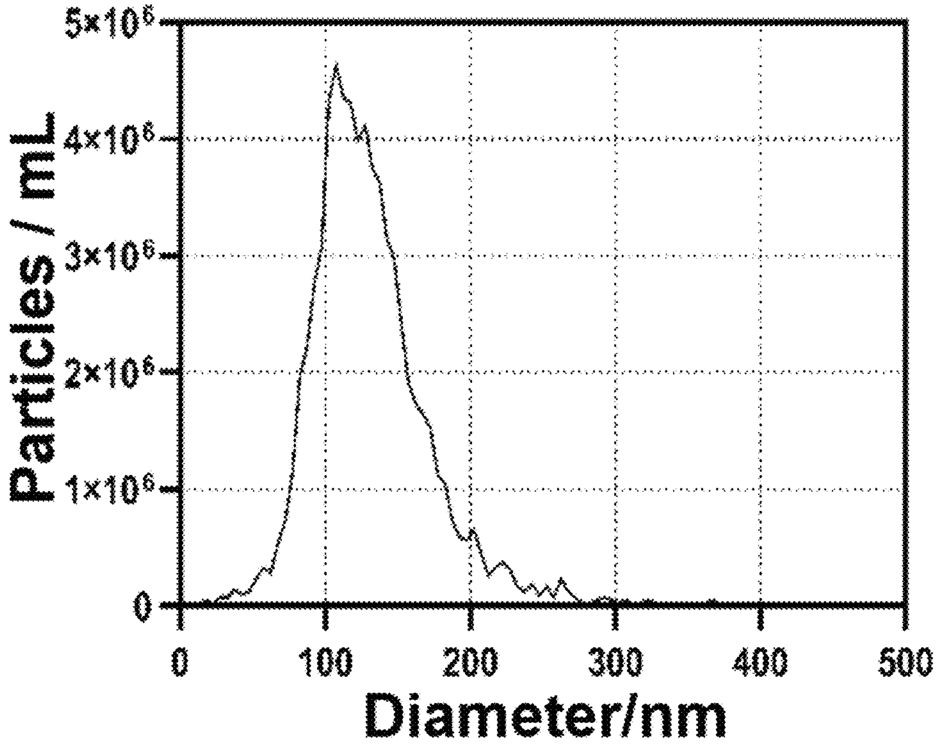
Figure 1C:
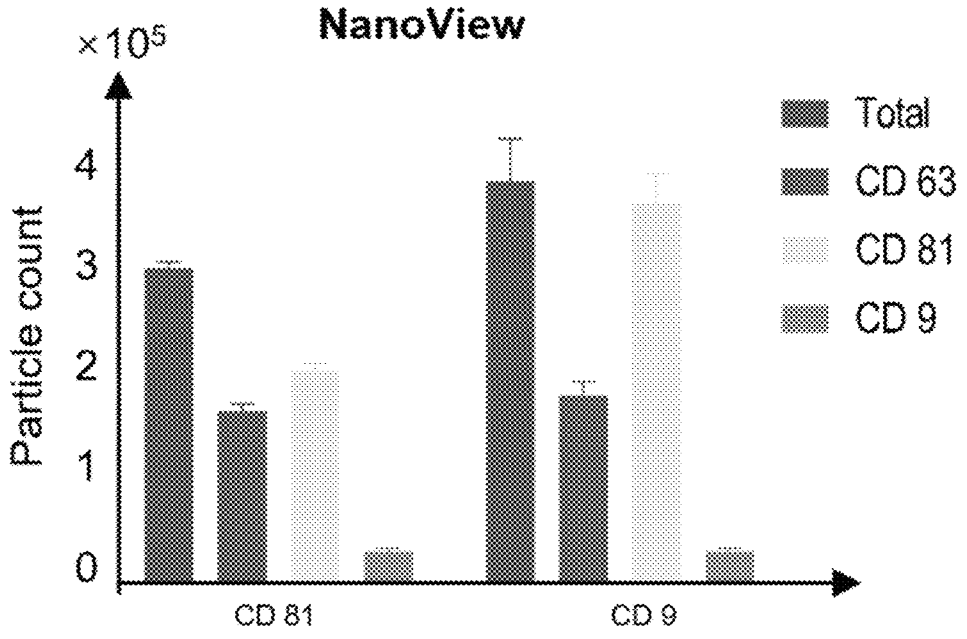
Figure 1D:
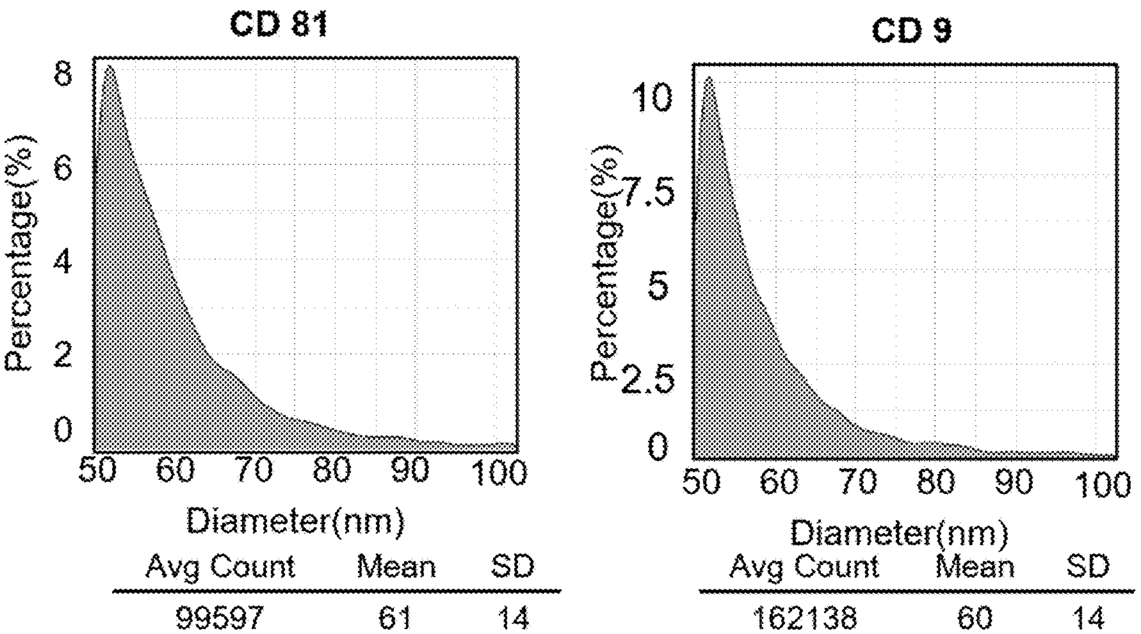
Figure 1E:
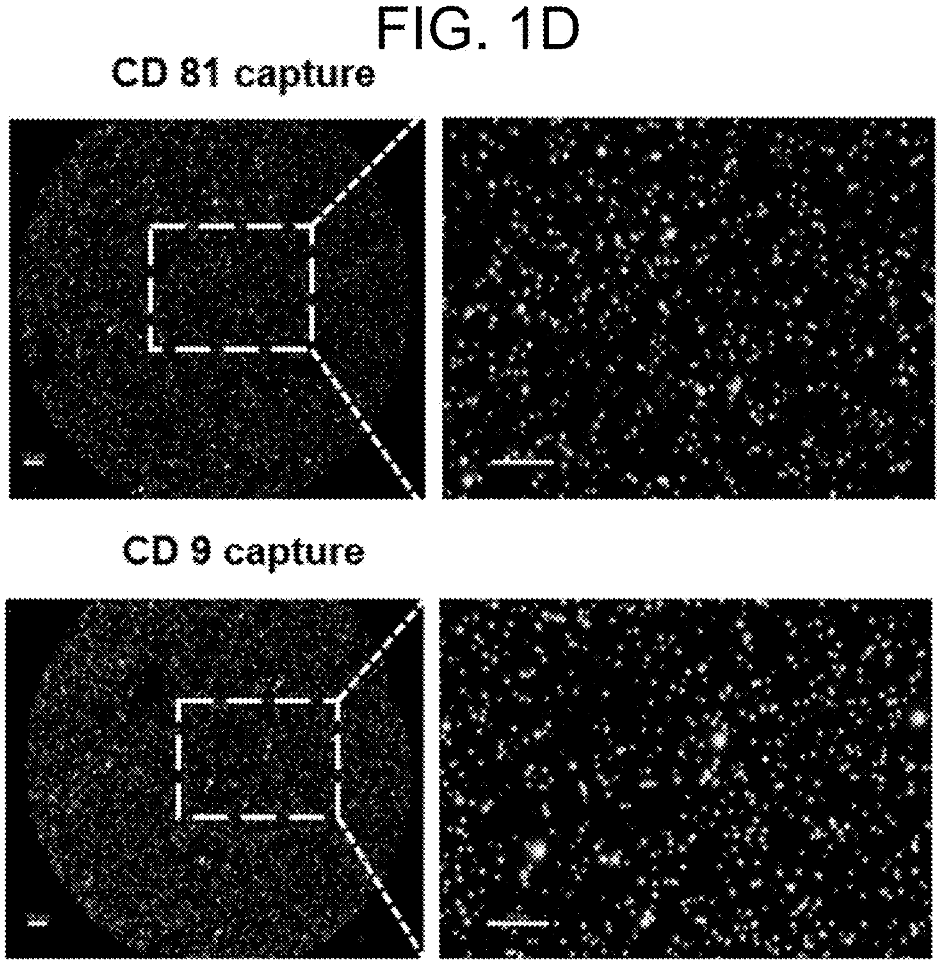
Figure 1F:
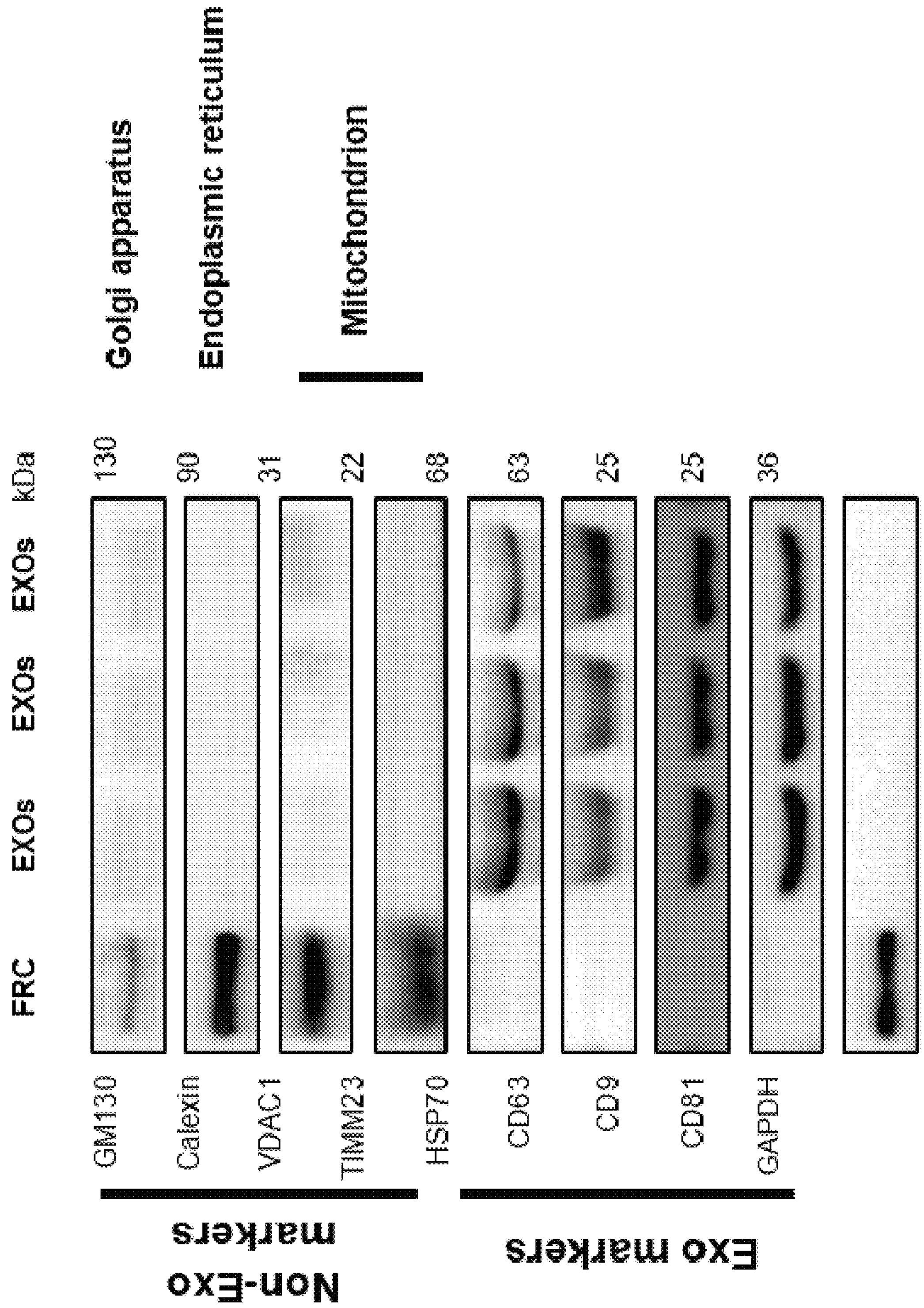
FIG. 1F: Western blot analysis of exosomes markers (HSP70, CD63, CD9, and CD81) and non-exosomal markers (GM130, calnexin, VDAC1, and TIM23) in FRCs and FRC-Exos.
Figure 2A:
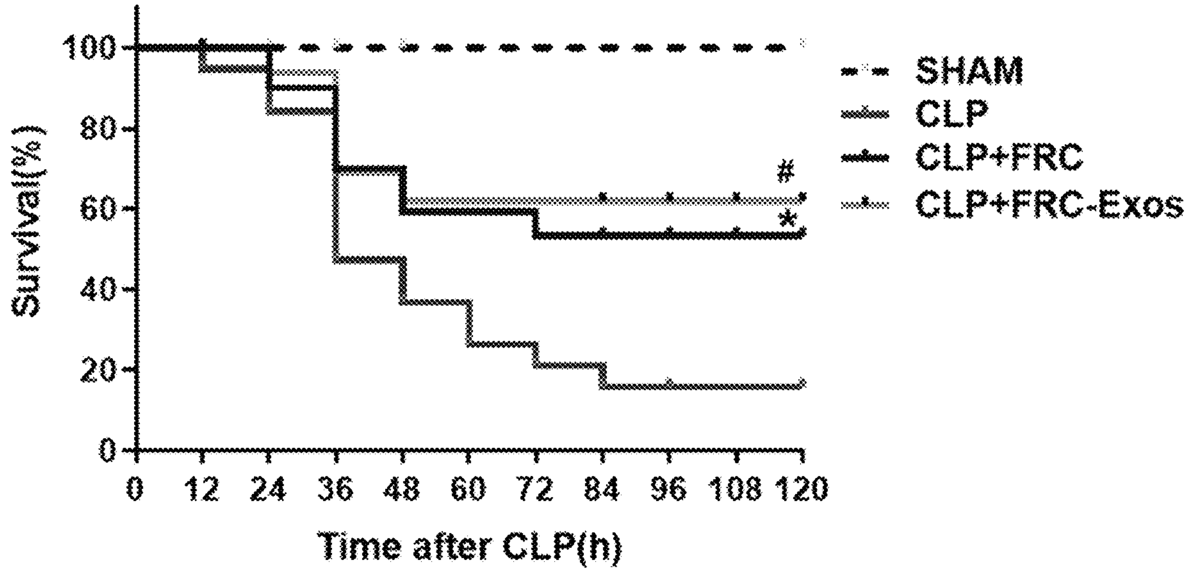
FIG. 2A-2E illustrate the protective effect of FRCs in the kidney against sepsis-associated damage through exosome secretion.

FIG. 2A: The survival rate of each group was recorded 120 hours after the surgery.

Figure 2B:
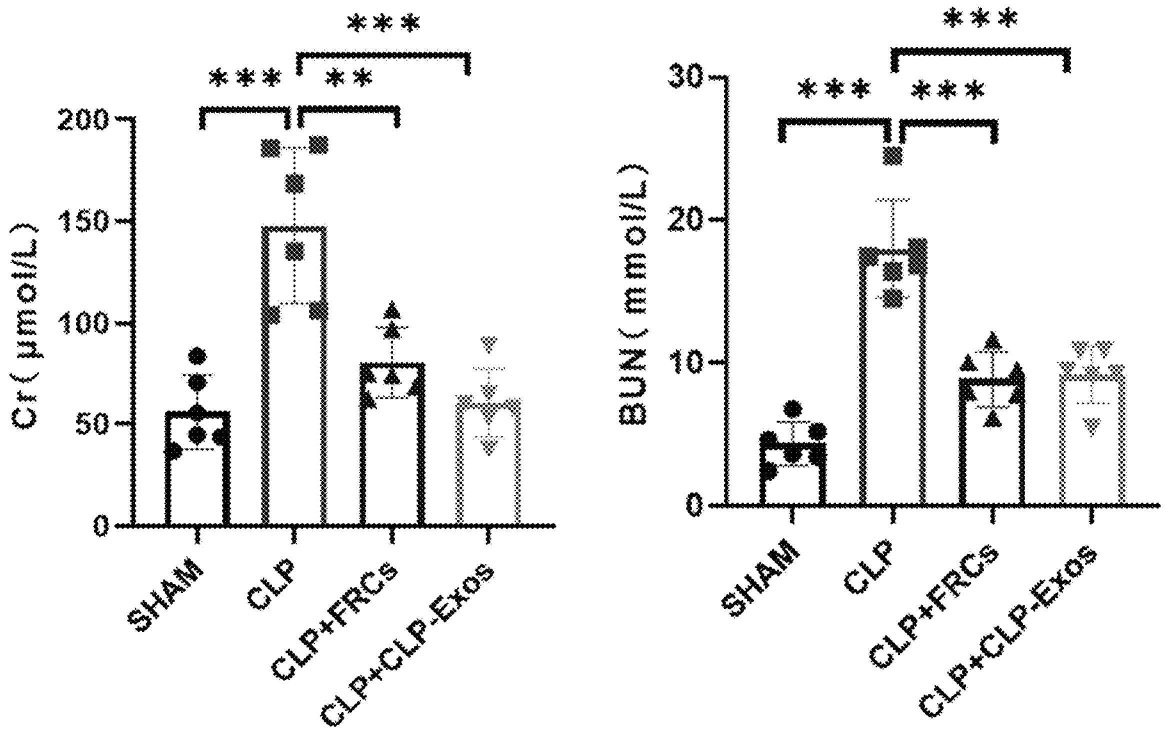
Figure 2C:
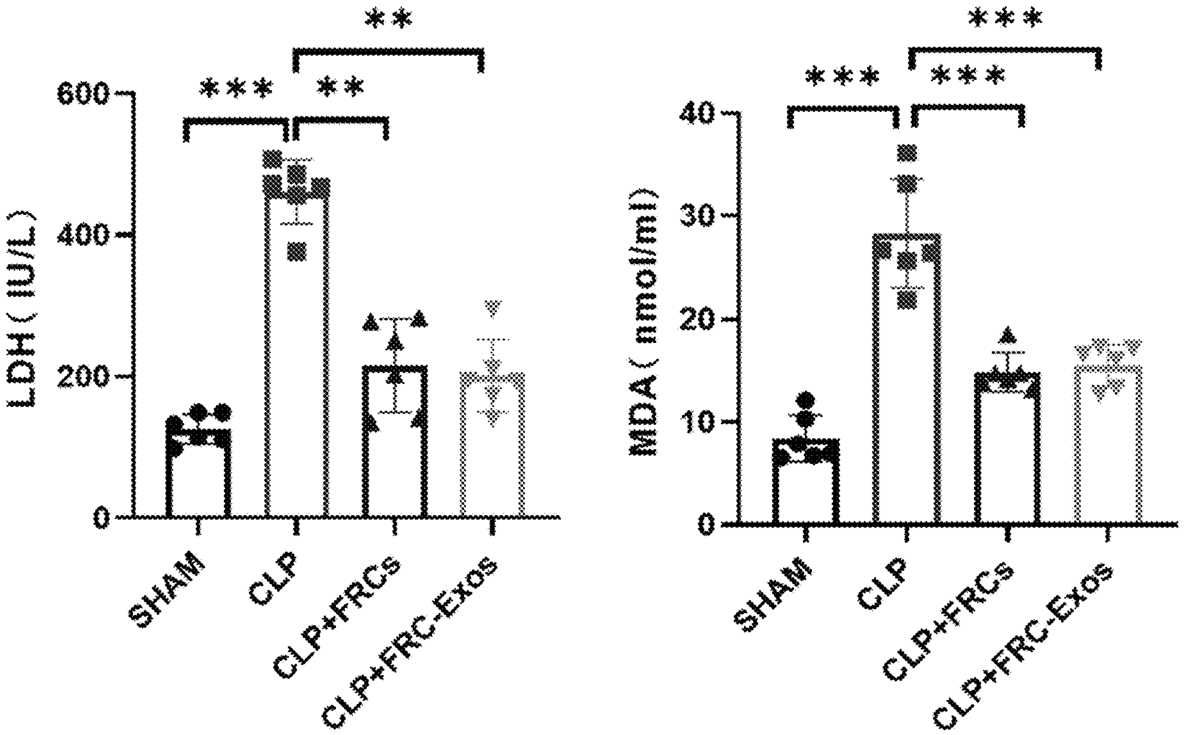
Figure 2D:
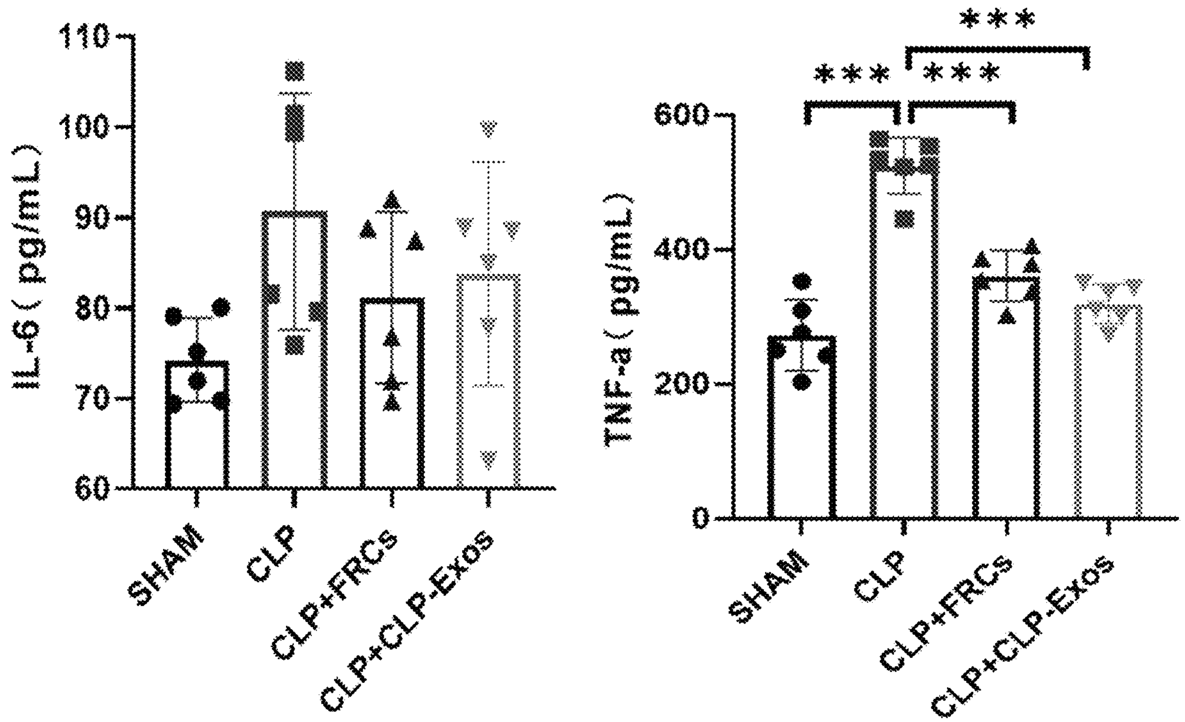

FIG. 2B-2D: The serum concentration of Cr, BUN, LDH, MDA, IL-6, and TNF-α was measured 48 hours after CLP.

Figure 2E:
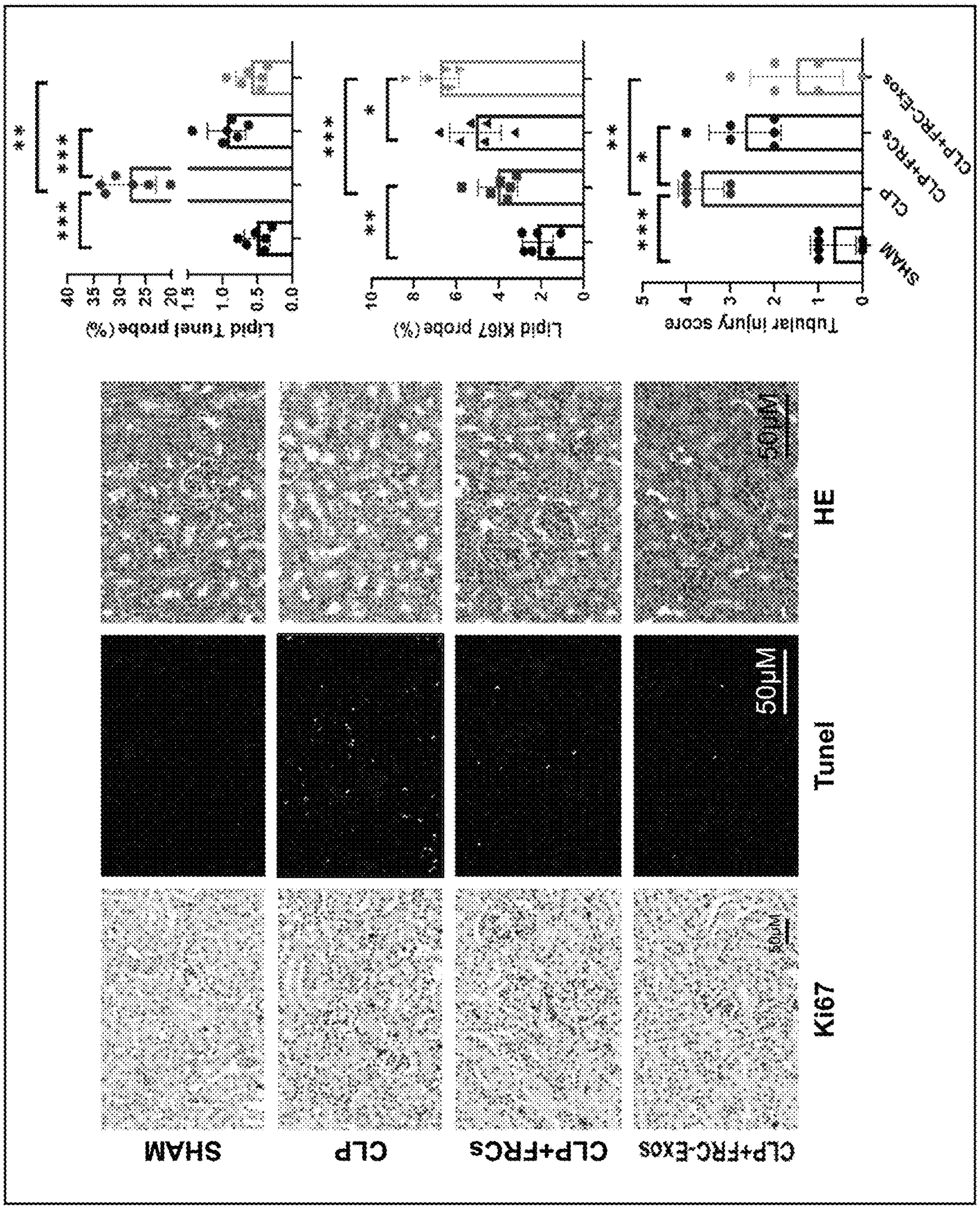

FIG. 2E: The apoptosis rate in the kidney was obtained by TUNEL analysis. Green dots indicate apoptotic cells. Scale, 50 μm. H&E staining was performed on kidney samples collected from the four groups. Scale, 50 μm. Immunohistochemical staining showed the optical microscopic image of the kidney tissue section of Ki67. Densely stained brown nuclei represent Ki67-positive cells. Scale, 50 μm.

Figure 3A:
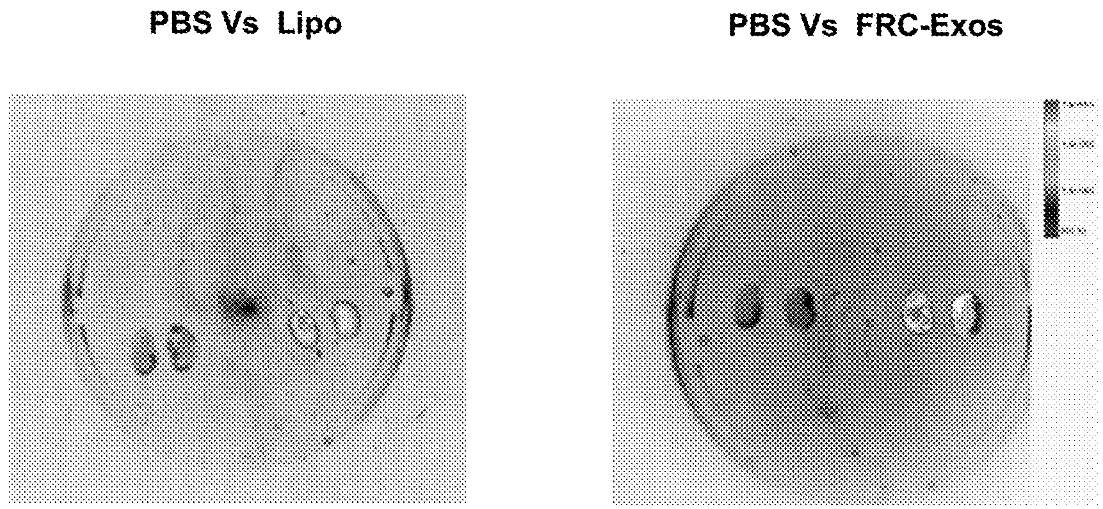
Figure 3B:
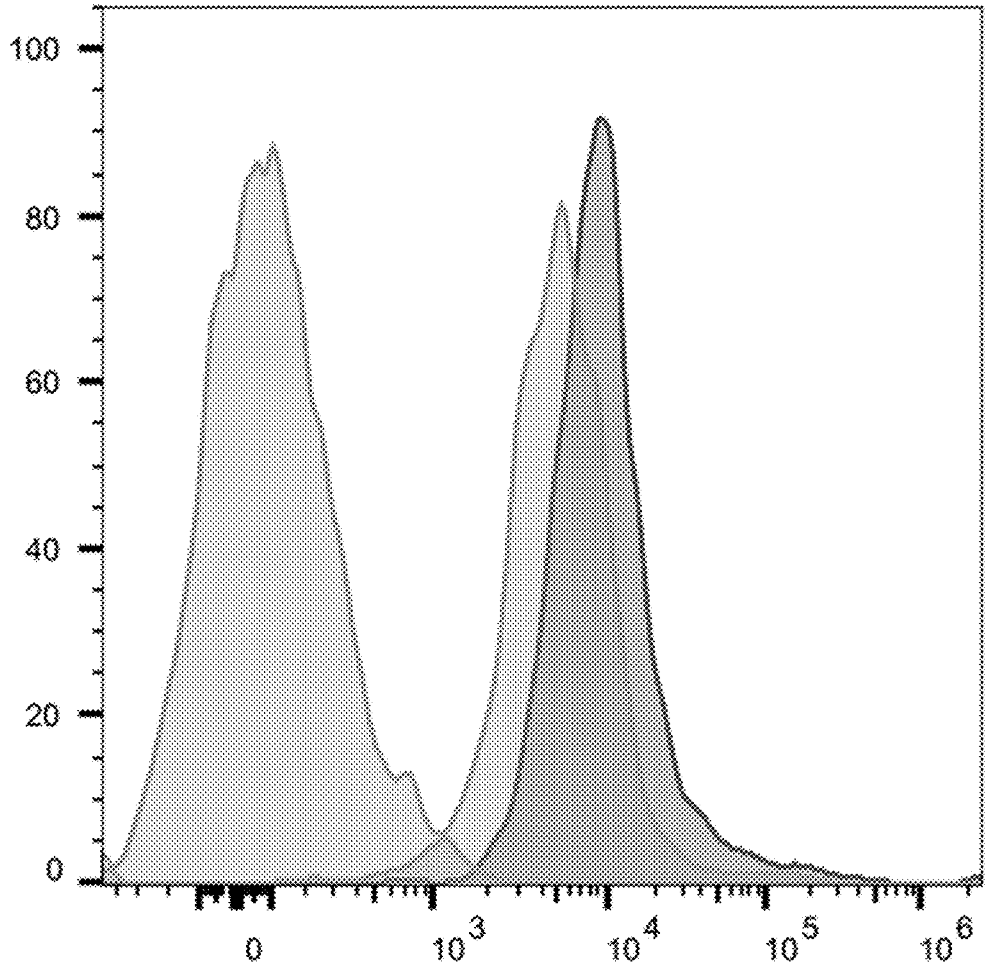
Figure 3C:
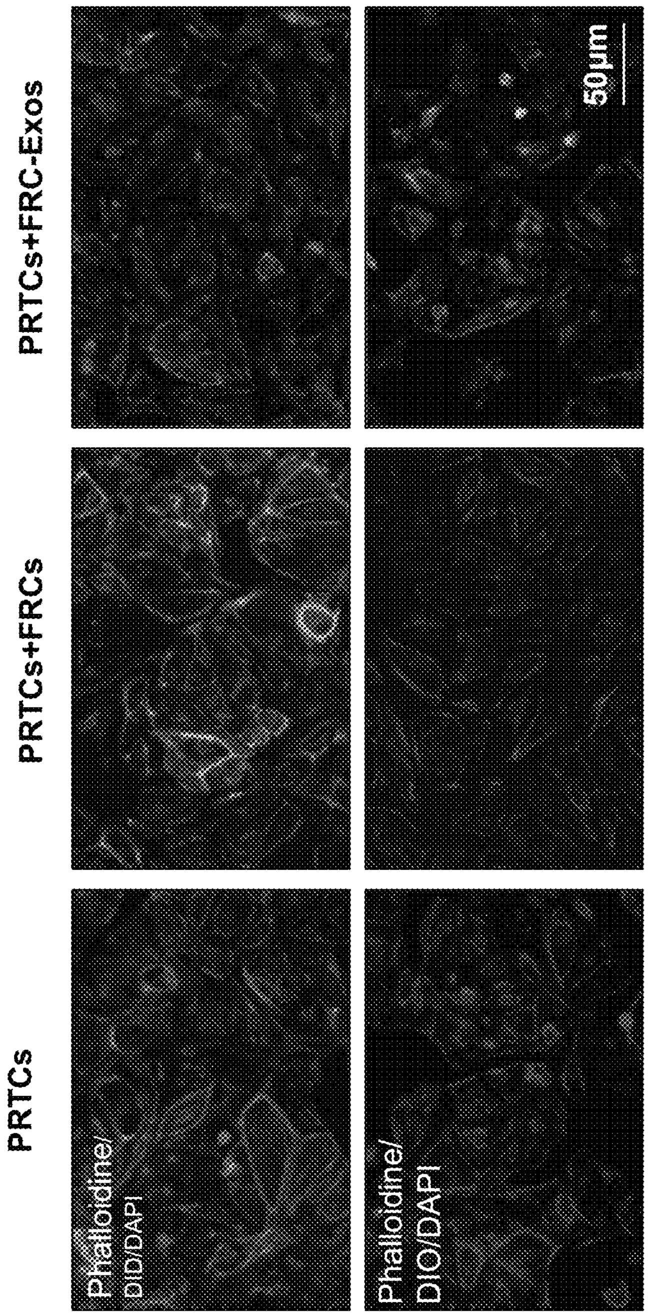

FIG. 3A-3C illustrate the results of targeting injured kidneys with Exos derived from FRCs.

FIG. 3A: Liposomes labeled with DiD and FRC-Exos were administered via caudal vein injection. In vivo imaging of the kidneys was performed 24 hours after CLP.

FIG. 3B: DiD fluorescence in kidney tissues was measured using flow cytometry.

FIG. 3C: In the FRC group, DiO/DiD-labeled FRCs were co-cultured with renal tubular cells in Transwell culture plates for 24 hours. In the FRC-Exos group, DiO/DiD-labeled FRC-Exos were added to PRTC medium and cells were cultured for 24 hours. Phalloidin staining was used to visualize the cytoskeleton of renal tubular cells, and DAPI was used to stain the cell nucleus. Red: DiD; Green: DiO. Fluorescence of the renal tubular cells was observed under confocal microscopy. Scale bar, 50 μm.

FIG. 4A-4J illustrate the outcome of FRC-Exos in limiting the activation of NLRP3 inflammasomes in S-AKI by promoting PINK1-dependent mitochondrial autophagy. The PRTCs were subjected to treatment with LPS (10 μg/ml) or LPS and FRC-Exos for a duration of 24 hours.

Figure 4A:
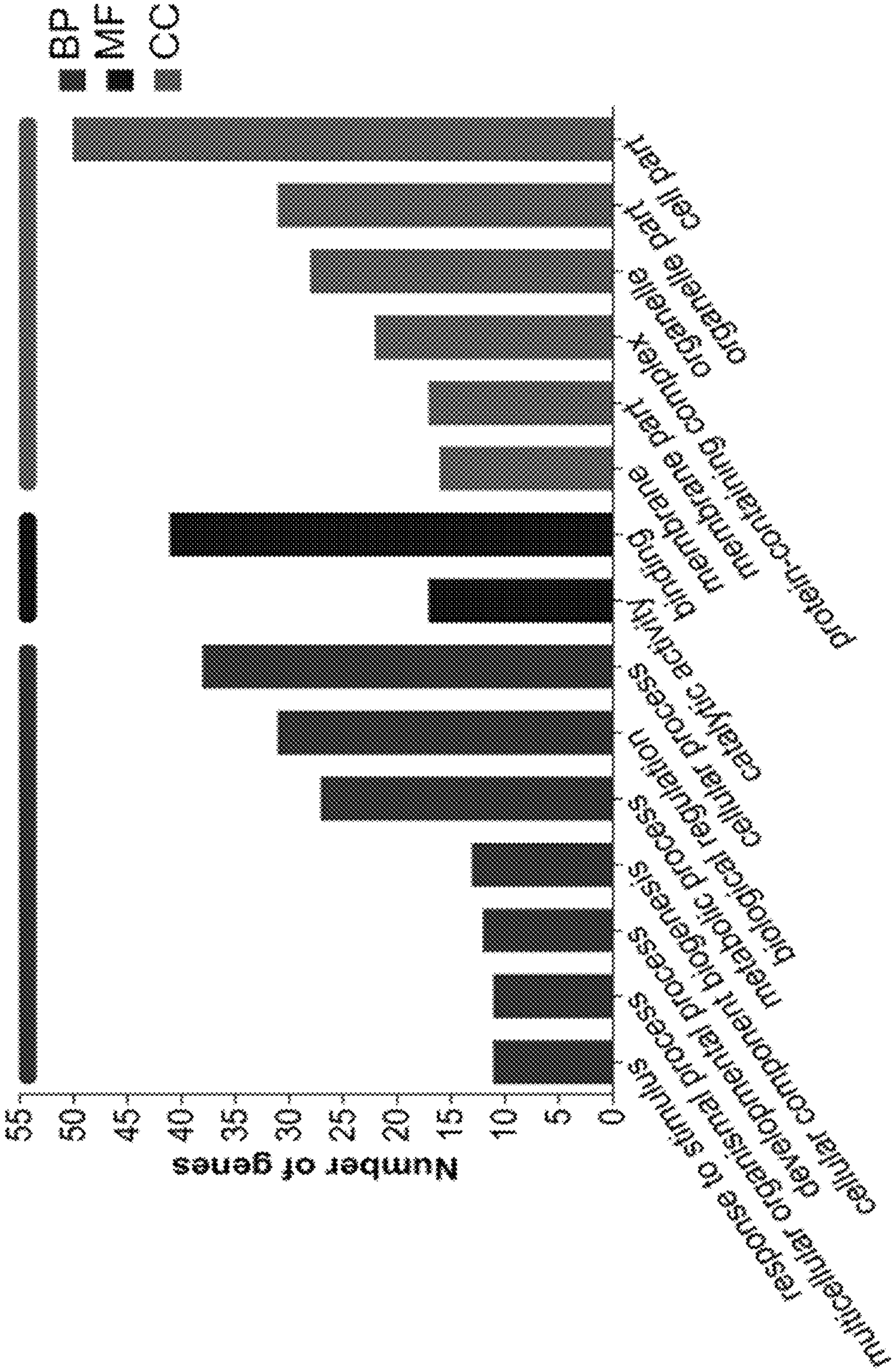

FIG. 4A: GO annotation analysis was performed on differentially expressed genes in renal cells treated with LPS and LPS FRC-Exos groups. BP refers to biological processes, MF refers to molecular functions, and CC refers to cellular components.

Figure 4B:
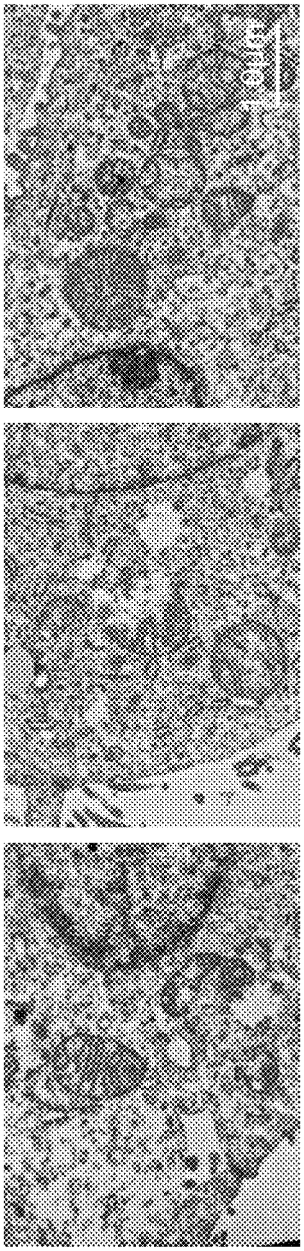

FIG. 4B: Changes in mitochondrial ultrastructure of PRTCs were observed using transmission electron microscopy. Scale bar: 1.0 micrometer.

Figure 4C:
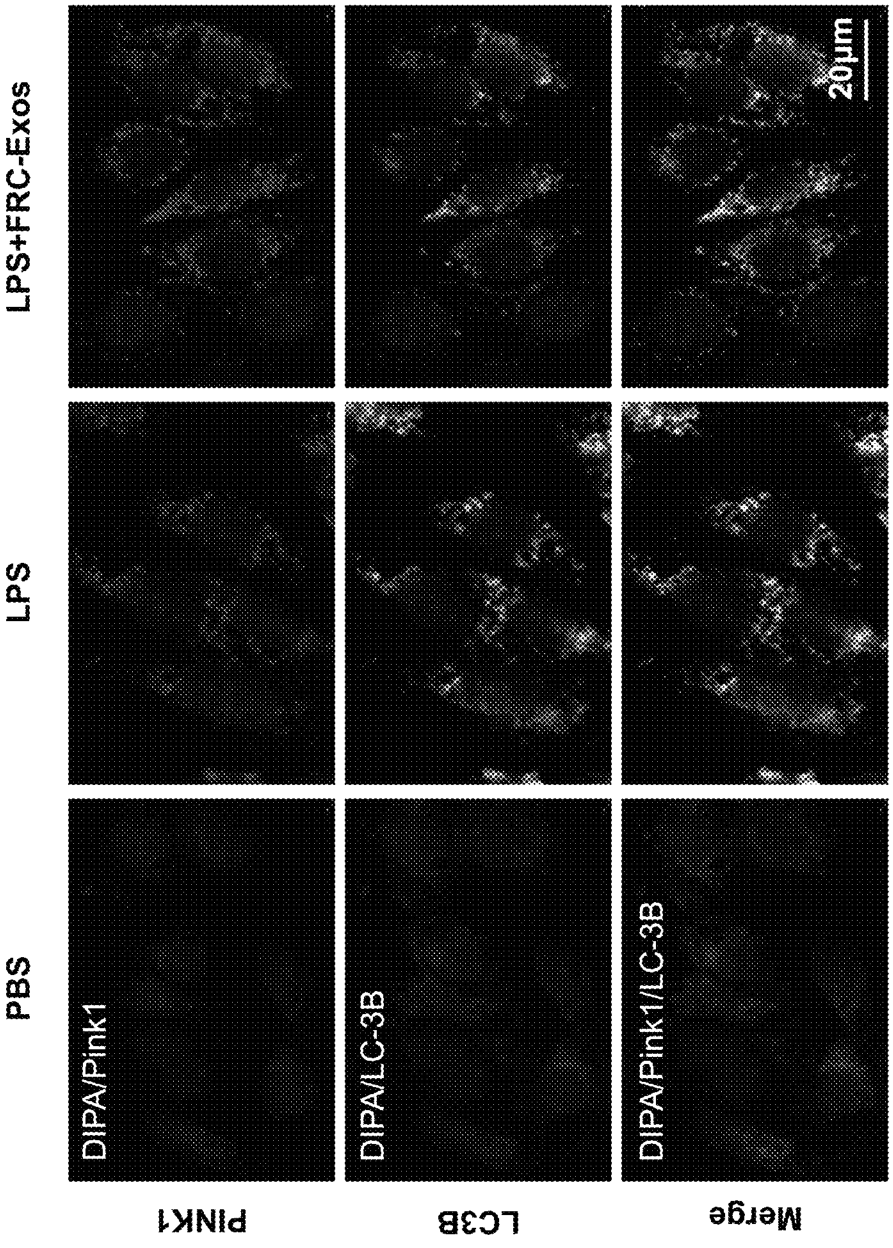

FIG. 4C: Immunofluorescence staining of PINK1 (red), LC3 (green), and nucleus (blue) was conducted in PRTCs. Scale bar: 10 micrometers.

Figure 4D:
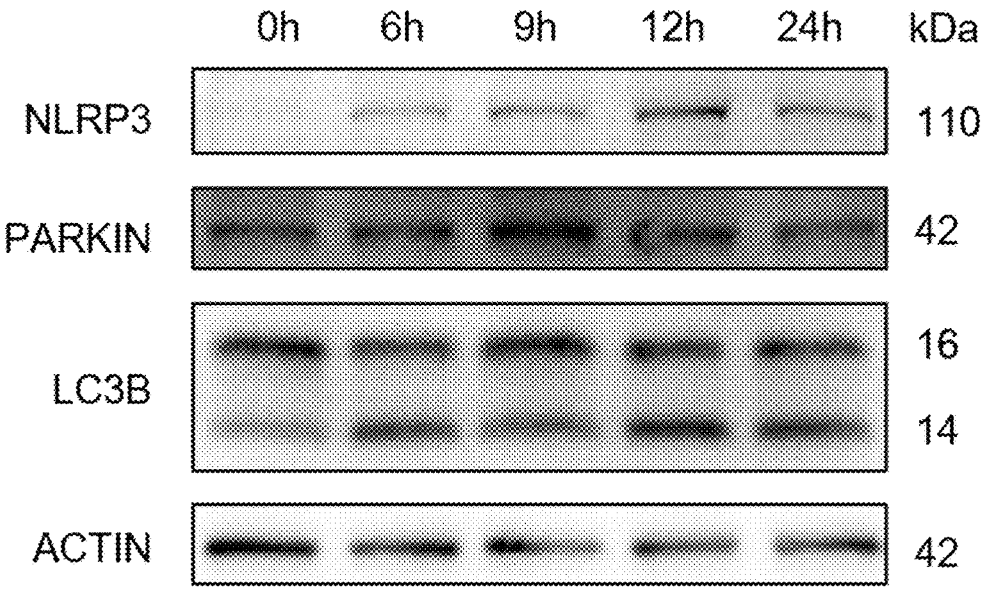

FIG. 4D: The levels of NLRP3, N-GSDMD, PINK1, P-PARKIN, and LC3 in PRTCs were analyzed using WB immunoblotting.

Figure 4E:
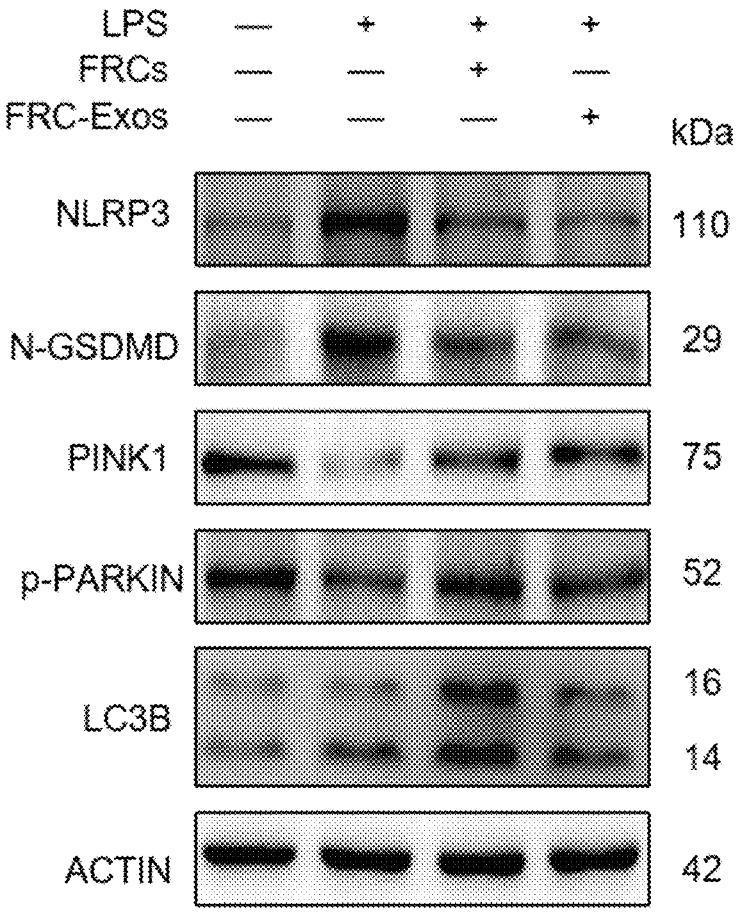

FIG. 4E: WB immunoblotting results depicting the expression of NLRP3, PARKIN, and LC3 in PRTCs at different time points after LPS (10 μg/ml) treatment.

Figure 4F:
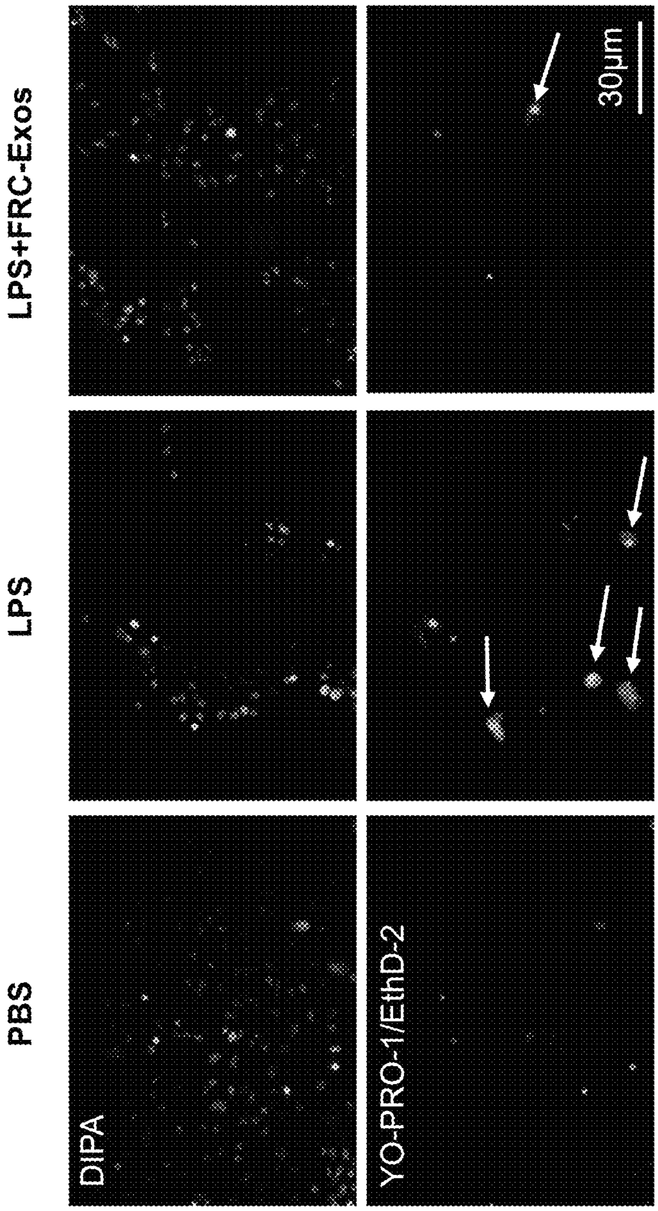

FIG. 4F: Fluorescence staining was performed using YO-PRO-1, Eth-D2, and DAPI. YO-PRO-1 represents apoptotic cells, Eth-D2 represents dead cells, and DAPI stains the nucleus. Arrows indicate apoptotic cells. Scale bar: 1.0 micrometer.

Figure 4G:
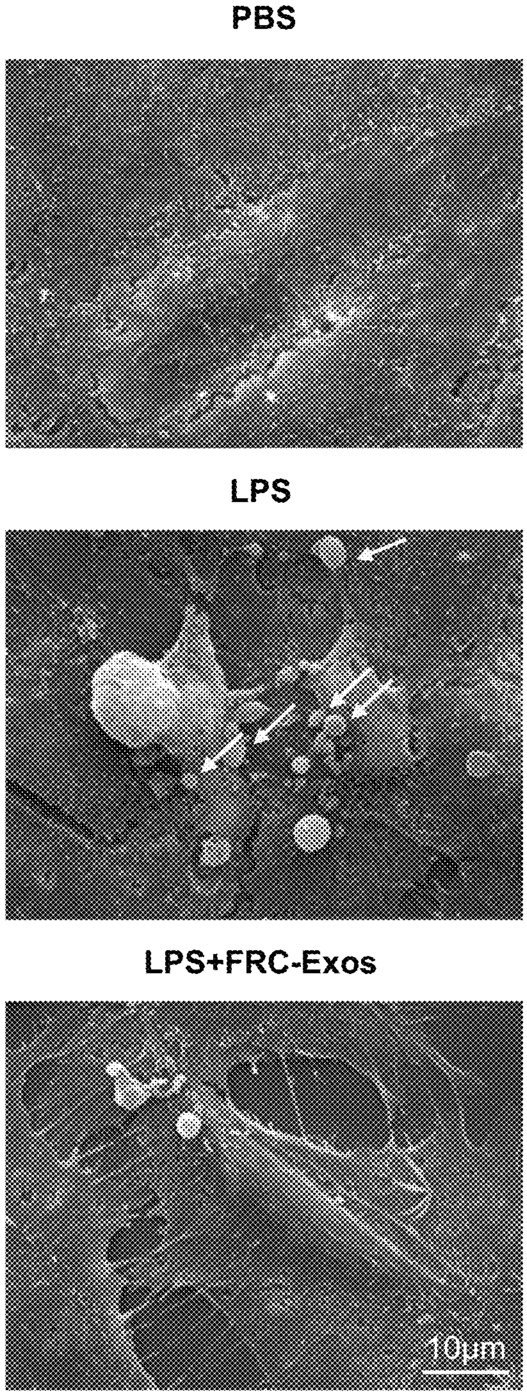

FIG. 4G: Morphology of PRTCs was observed using scanning electron microscopy. Scale bar: 50 micrometers.

Figure 4H:
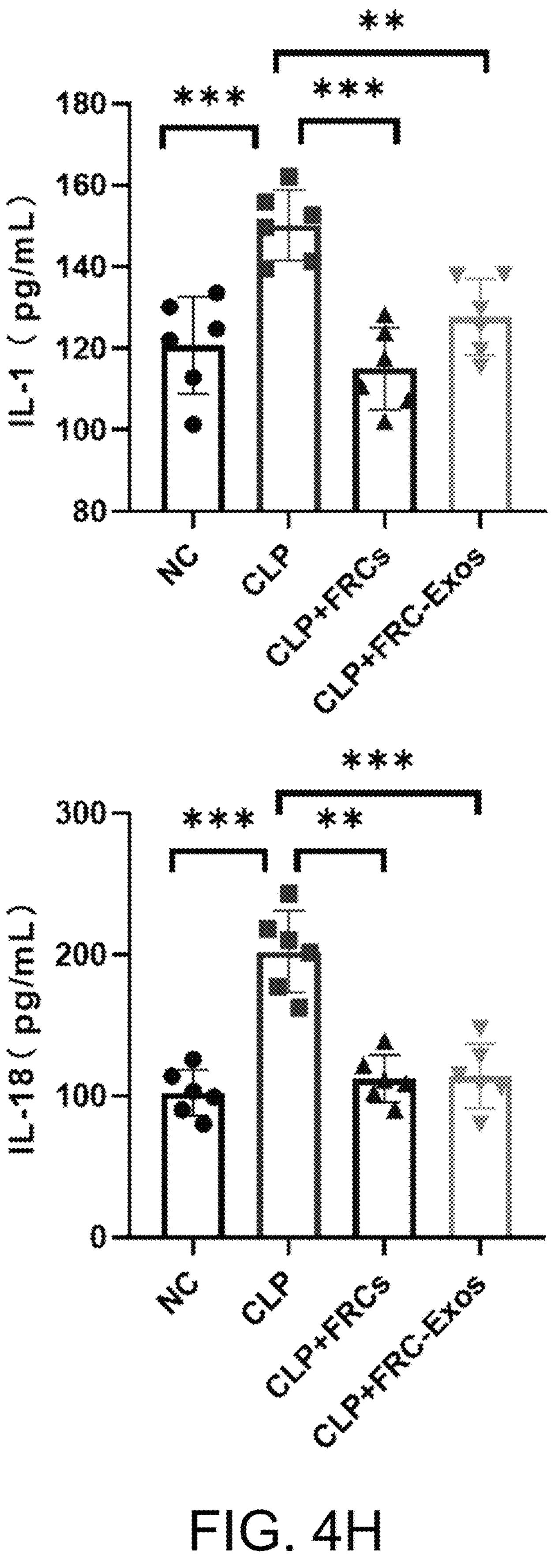
Figure 4I:
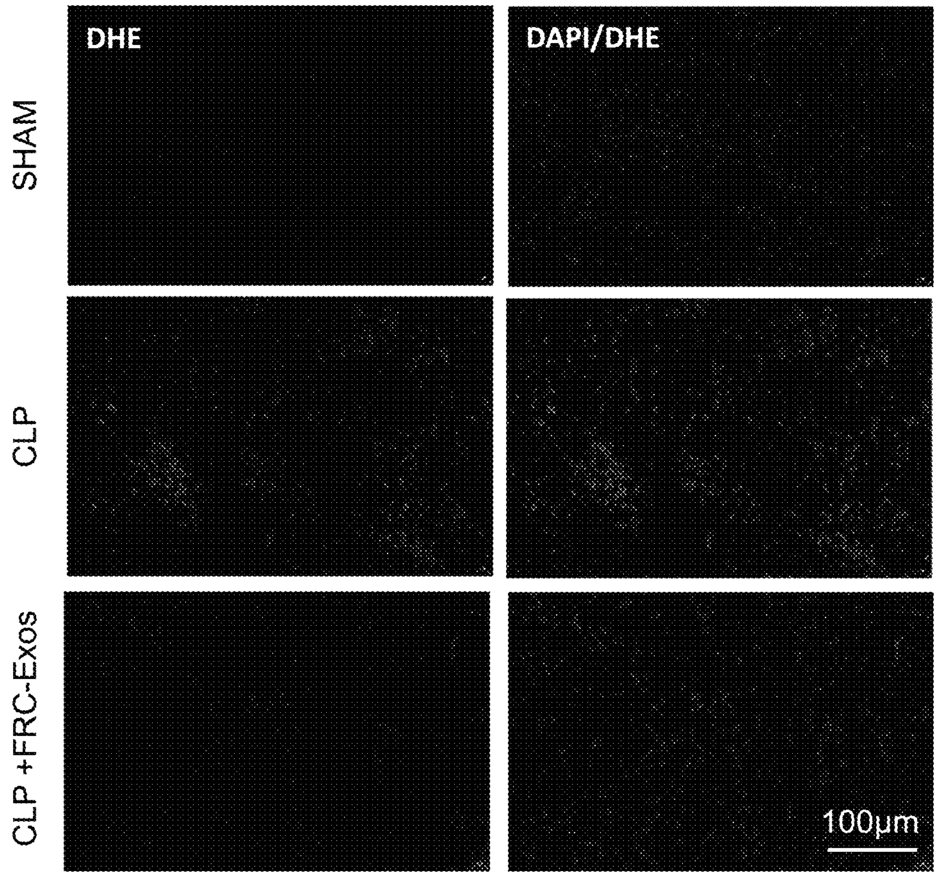
Figure 4J:
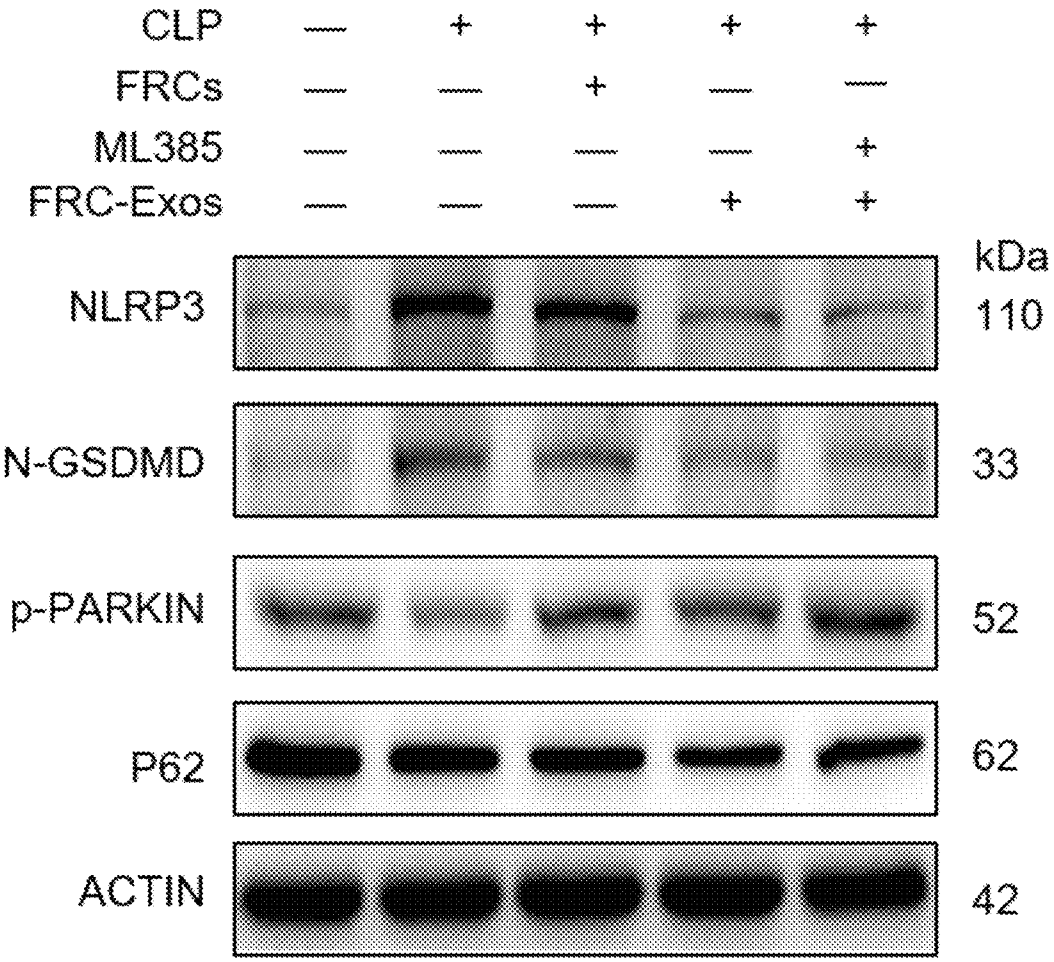

FIG. 4H-4J: FRC-Exos were intravenously injected into C57BL/6 mice 1 hour after CLP. Kidney tissue and serum were collected 24 hours post-CLP. h. Levels of IL-1 and IL-18 in serum were measured using ELISA. All statistical tests used in FIG. 4I are two-sided, and a two-sided P-value<0.05 was considered statistically significant. p≤0.01. *p≤0.001. j. DHE staining was performed to label superoxide dismutase (O2-). DHE staining of kidney tissue is shown. j. ML385 was injected 1 hour before the CLP procedure. WB immunoblotting analysis was performed for NLRP3, N-GSDMD, P-PARKIN, and P62 in kidney tissue.

FIG. 5A-5F illustrates the results of anti-inflammatory protein LTH-FRC-Exos improving septic kidney injury through CD5L.

Figure 5A:
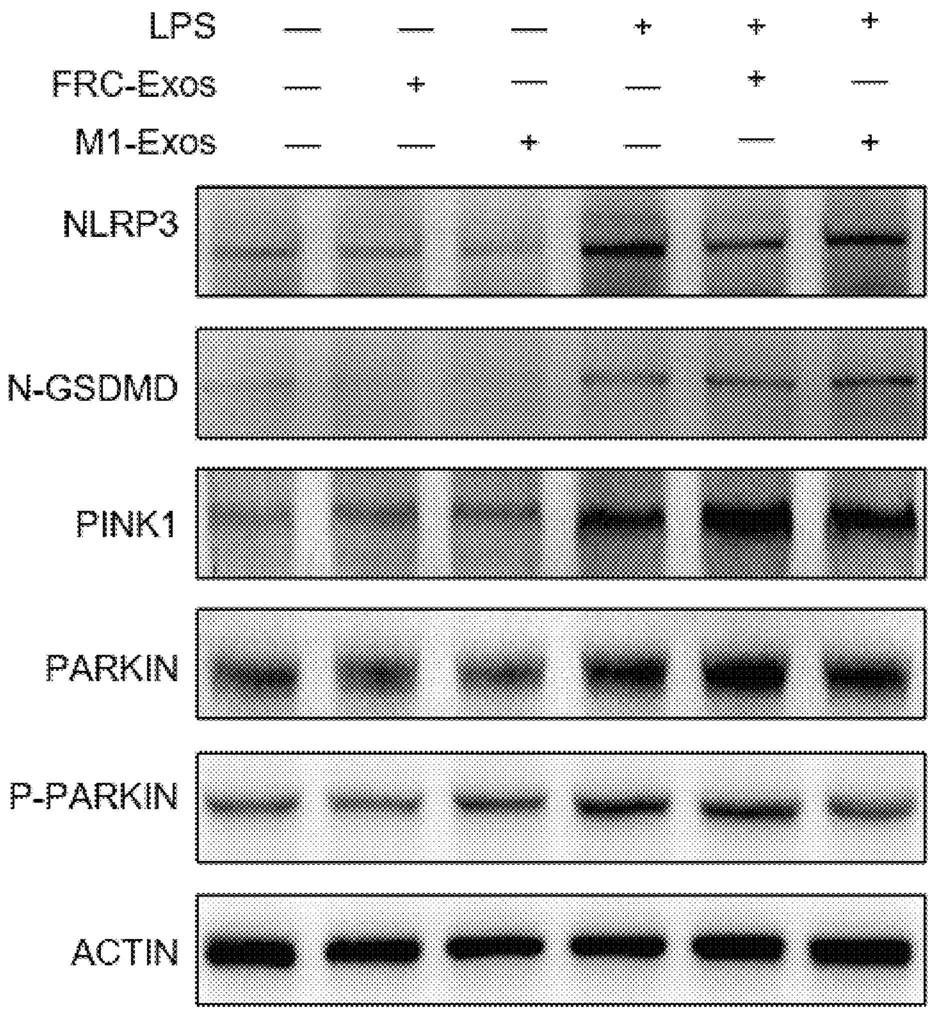

FIG. 5A: Represents immunoblot results of NLRP3, N-GSDMD, PINK1, PARKIN, and P-PARKIN in PRTCs following specified treatments.

Figure 5B:
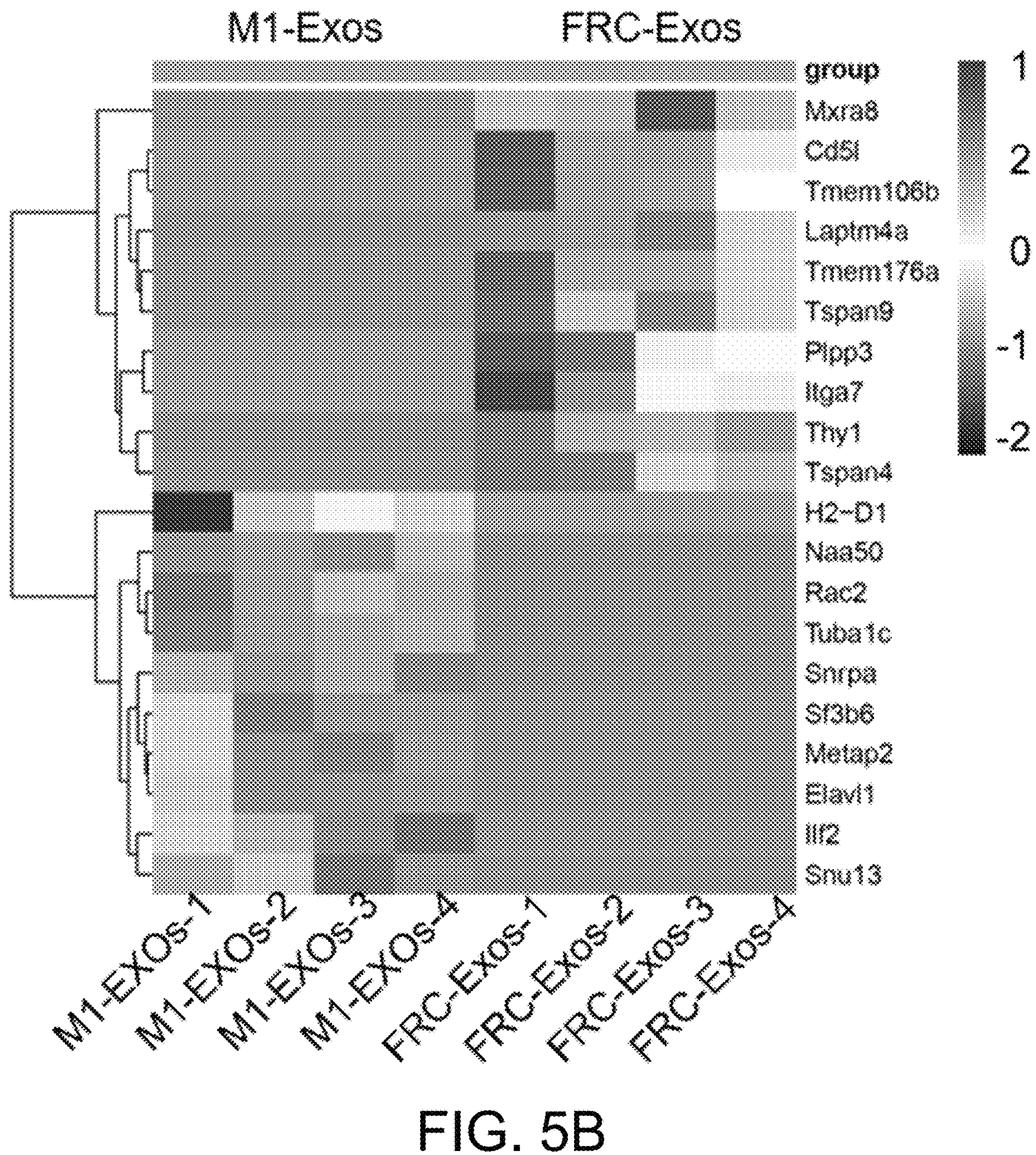

FIG. 5B: Heatmaps depicted differential expression of proteins in FRC-Exos and M1-Exos. Only the top 20 proteins are shown. Minimal protein abundance values were allocated for easier statistical analysis and visualization.

Figure 5C:
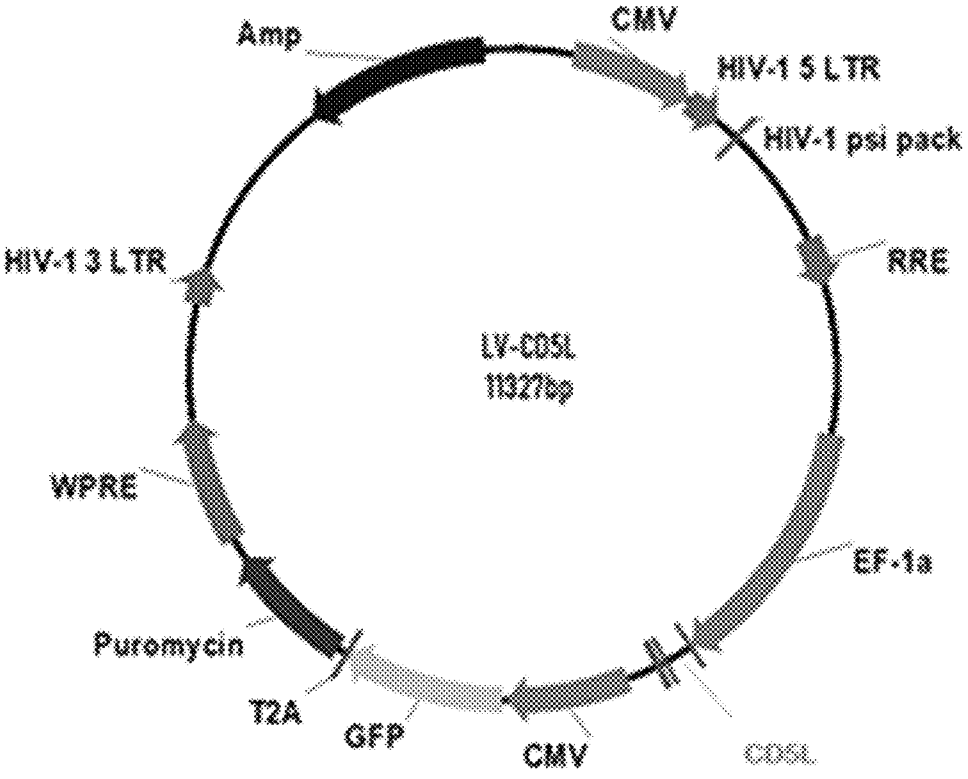

FIG. 5C: Plasmid map of CD5L.

Figure 5D:
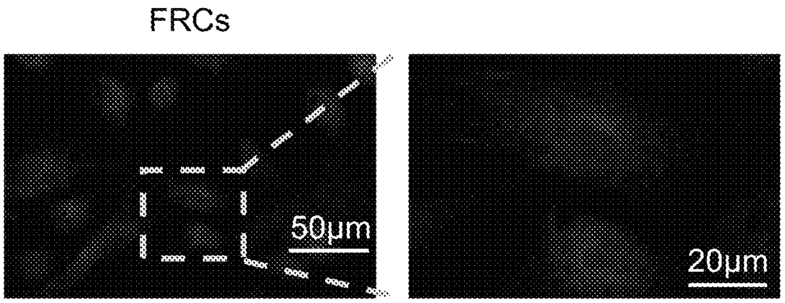

FIG. 5D: Immunofluorescence images of PRTCs stained with CD5L antibody (in red). Left, scale bar: 50 μm. Right, scale bar: 20 μm.

Figure 5E:
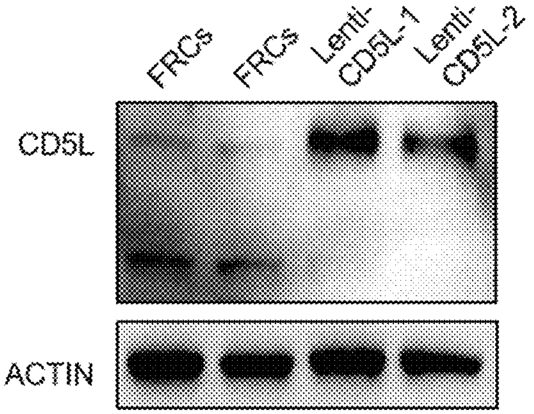

FIG. 5E: Western Blot analysis reveals the expression level of CD5L in FRC cells.

Figure 5F:
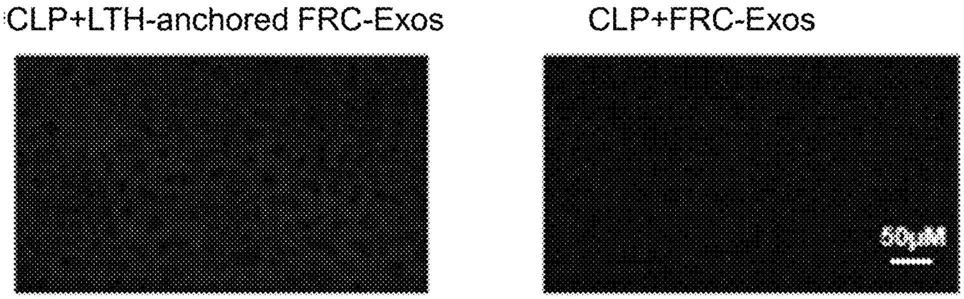

FIG. 5F: Fluorescence microscopy observation of kidney tissue slices labeled with DiR fluorescence.

FIG. 6A-6H illustrates the effectiveness of modified extracellular vesicles with specific targeting to the kidney in alleviating sepsis-associated renal injury.

Figure 6A:
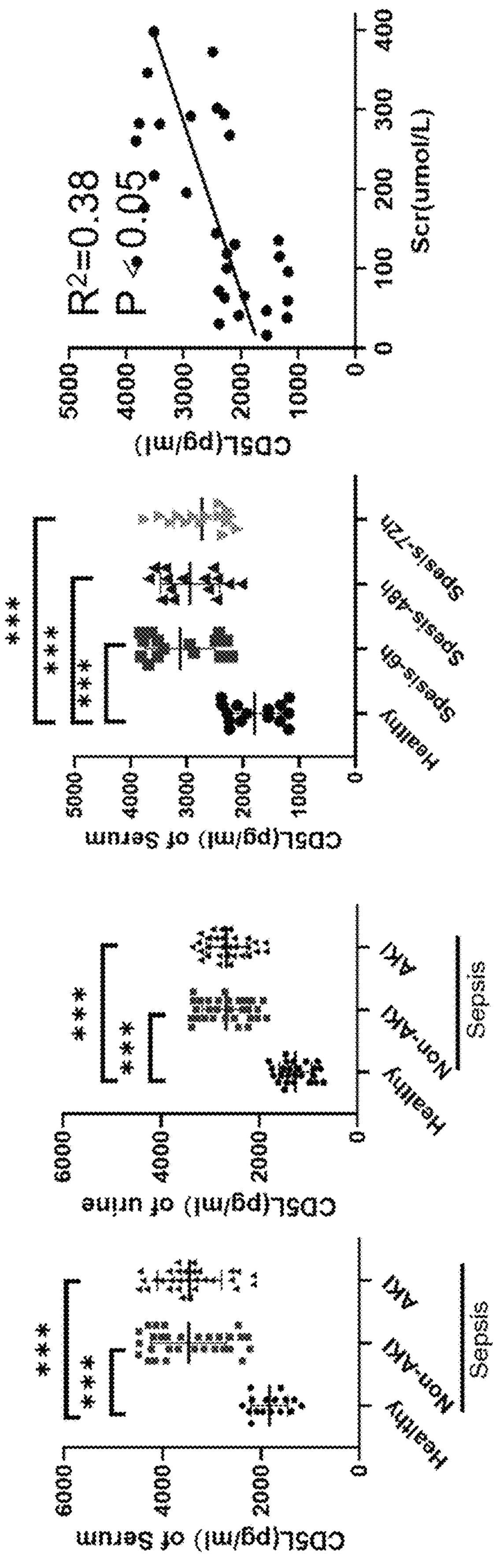

FIG. 6A: CD5L concentration was measured in serum or urine samples of septic and healthy control groups using an ELISA kit. Linear regression analysis was performed to determine the correlation between serum CD5L levels and creatinine.

FIG. 6B-6H: Wild-type (WT) mice underwent CLP surgery and were administered recombinant CD5L (rCD5L), CD5L-293T-Exos, or CD5L-FRC-Exos via tail vein injection. Kidney tissue and serum were collected 24 hours after CLP.

Figure 6B:
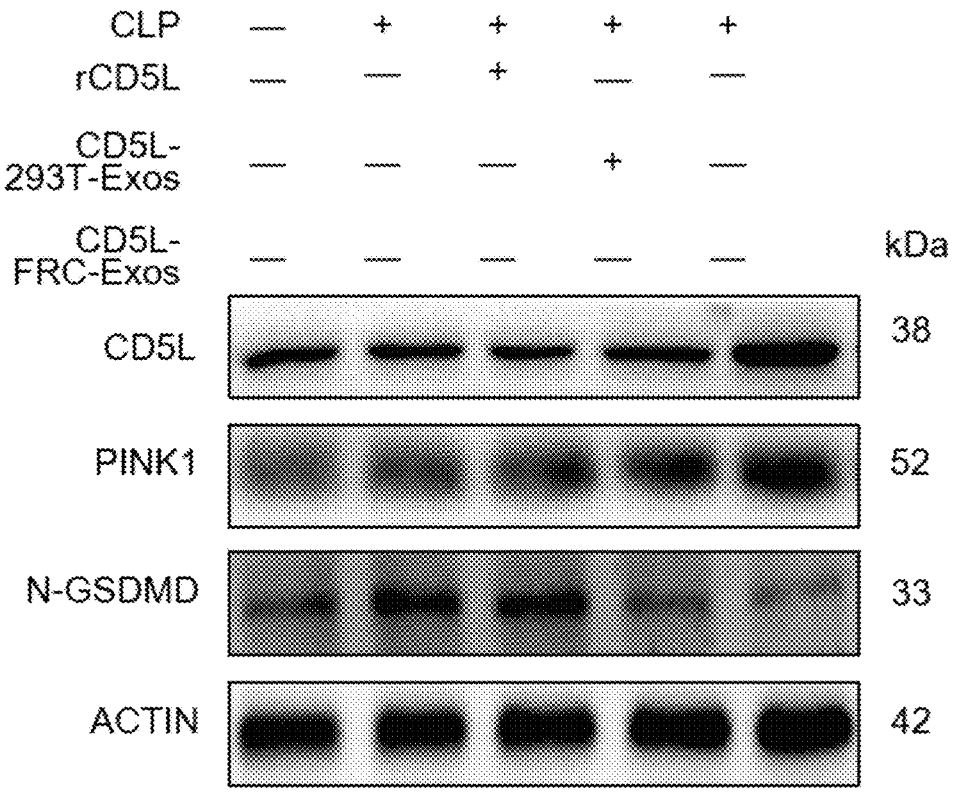

FIG. 6B: Western blot was conducted to detect CD5L, PINK1, and N-GSDMD levels in mouse kidney tissues from different groups. The survival rate of each group of mice was observed.

Figure 6C:
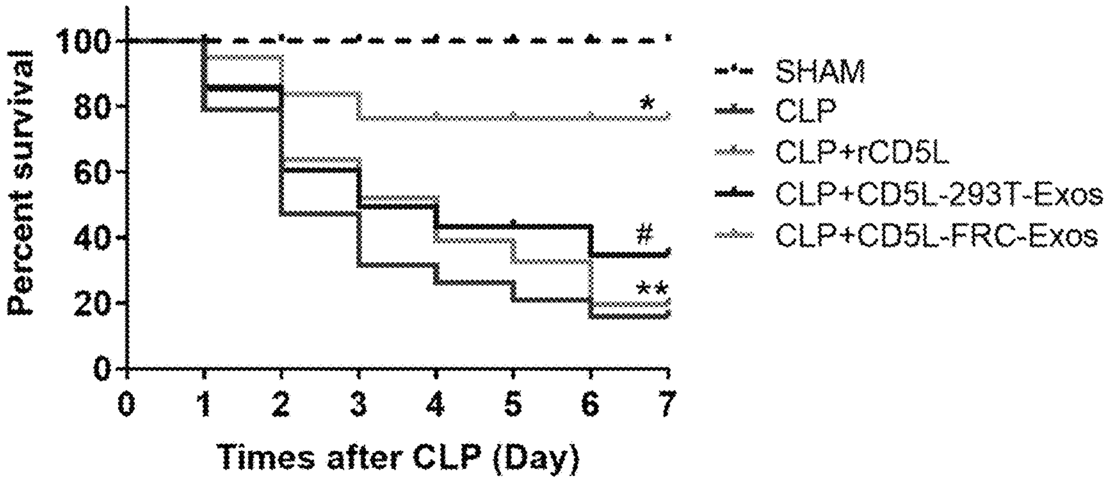

FIG. 6C: Survival rates at day 7 after CLP surgery. *p<0.05, CLP+CD5L-FRC-Exos compared to CLP+rCD5L; **p<0.01, CLP+CD5L-FRC-Exos compared to CLP; #p<0.05, CLP+CD5L-FRC-Exos compared to CLP+CD5L-293T-Exos. SHAM, n=12; CLP, n=19; CLP+rCD5L, n=20; CLP+CD5L-293T-Exos, n=21; CLP+CD5L-FRC-Exos, n=20.

Figure 6D:
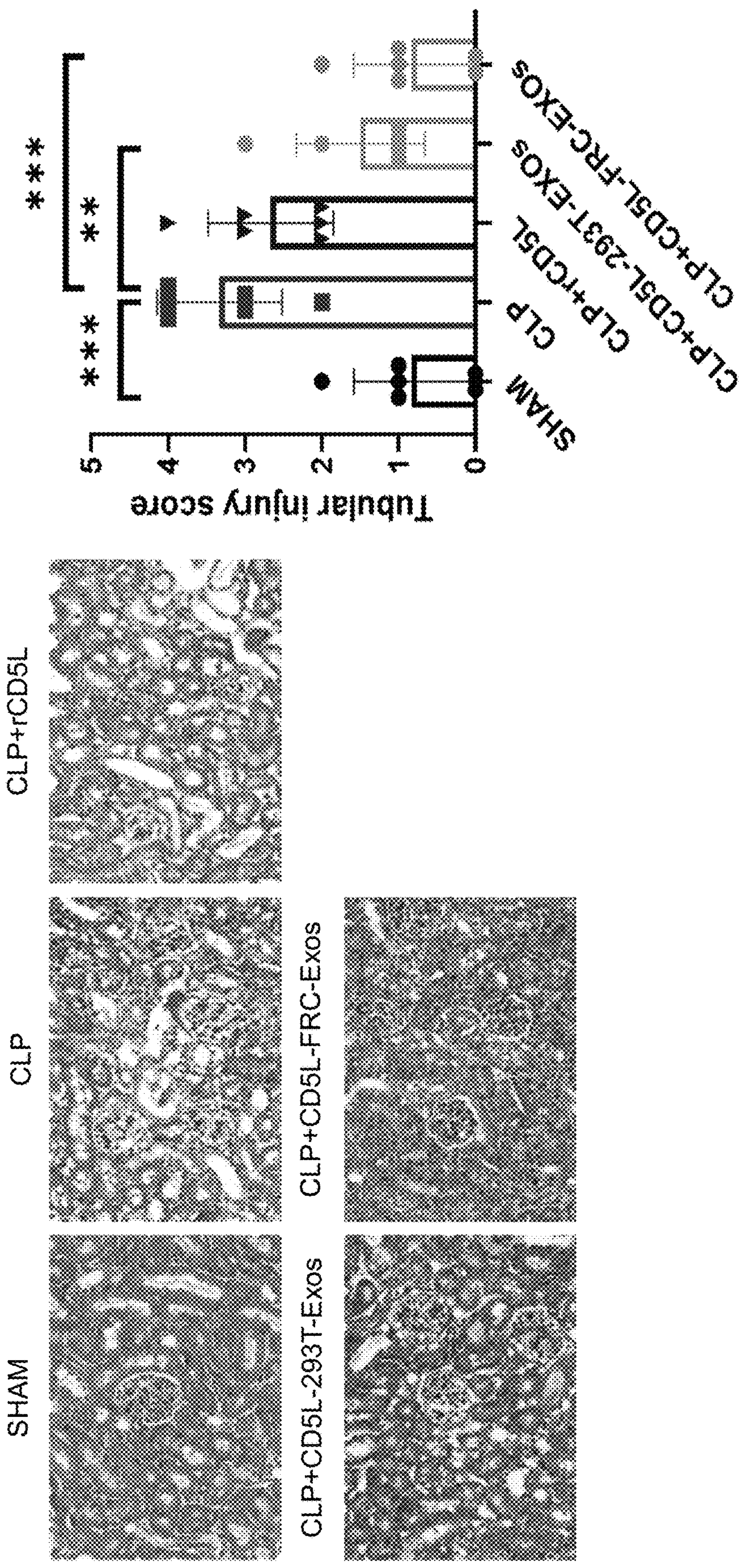

FIG. 6D: Kidney tissue histology stained with H&E.

Figure 6E:
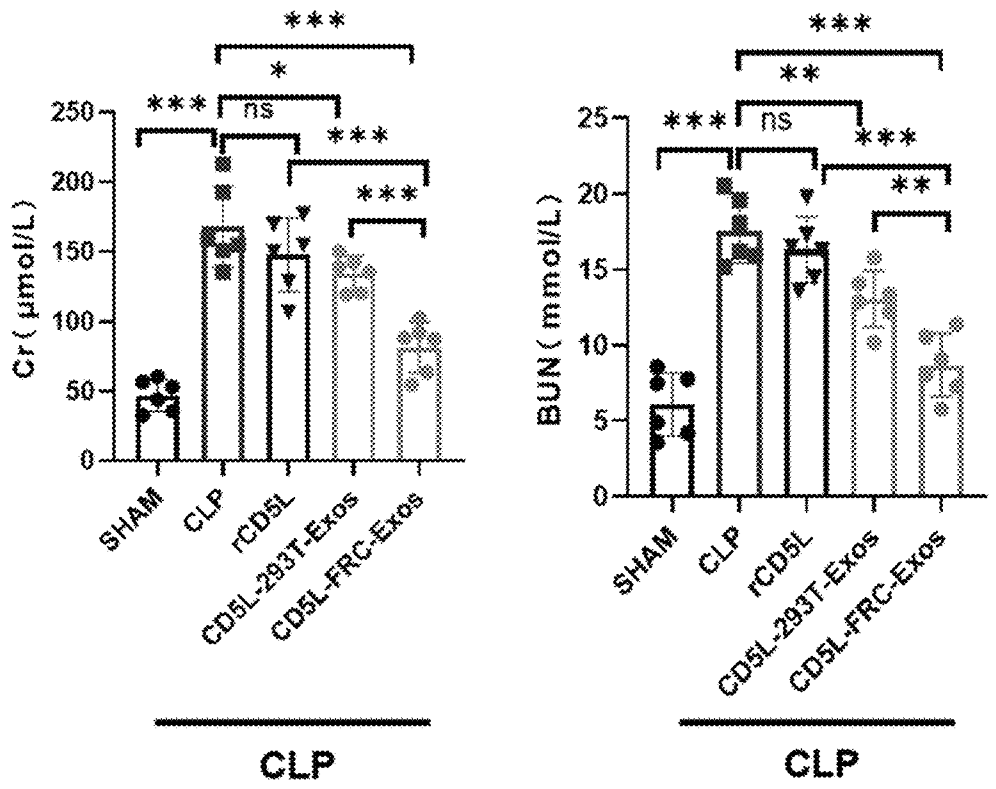
Figure 6F:
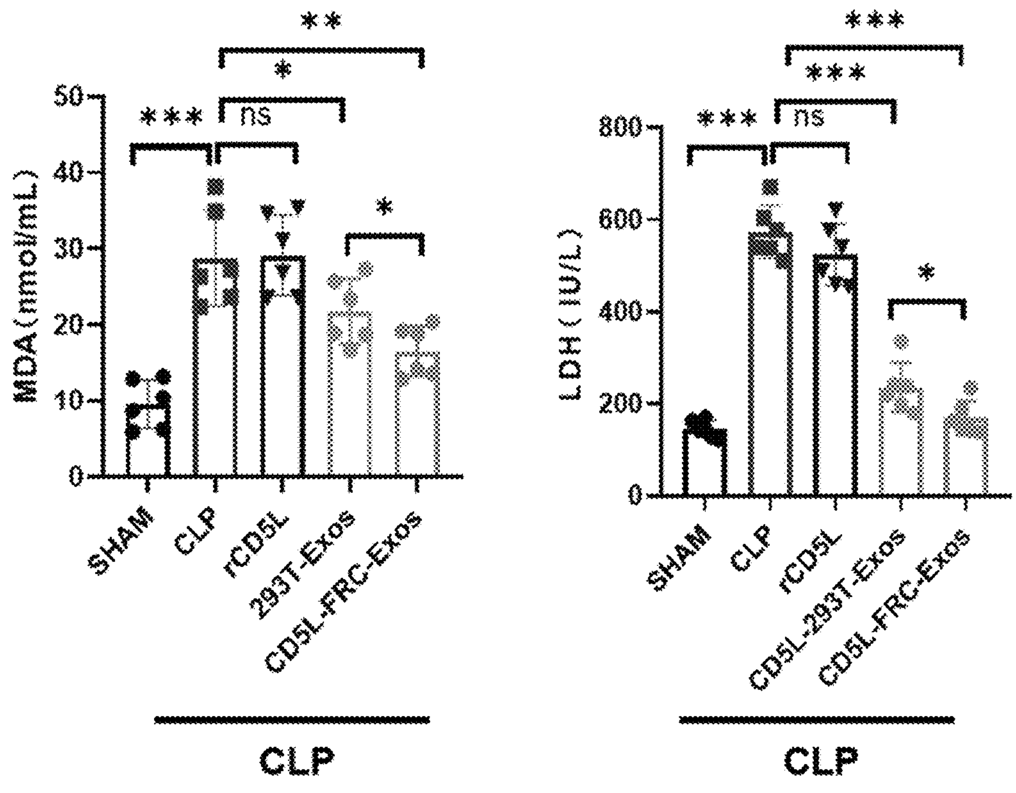

FIG. 6E, 6F: Measurement of Scr, BUN, MDA, and LDH levels.

Figure 6G:
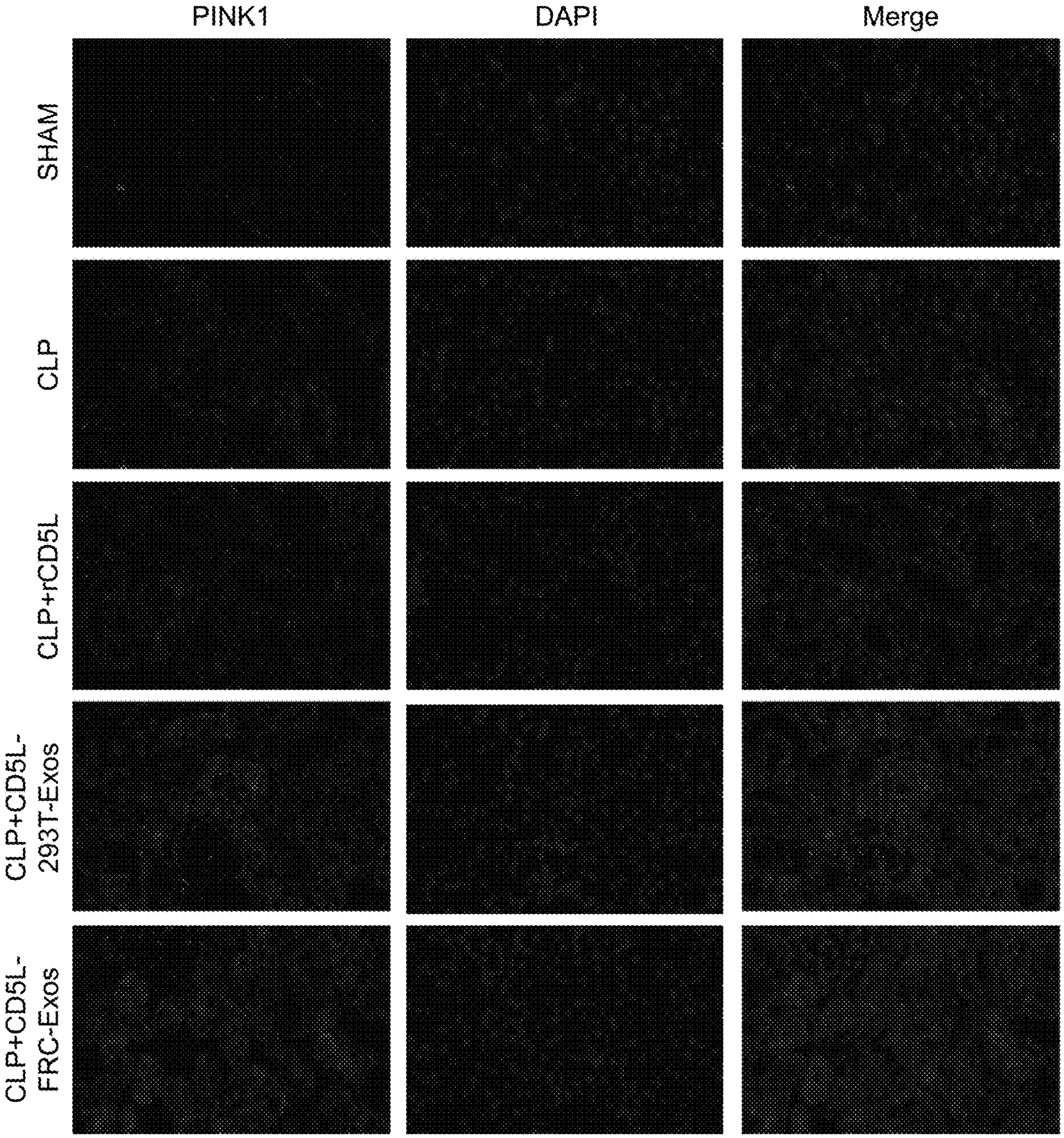

FIG. 6G: Immunofluorescence observation of PINK1 content in mouse kidney tissue.

Figure 6H:
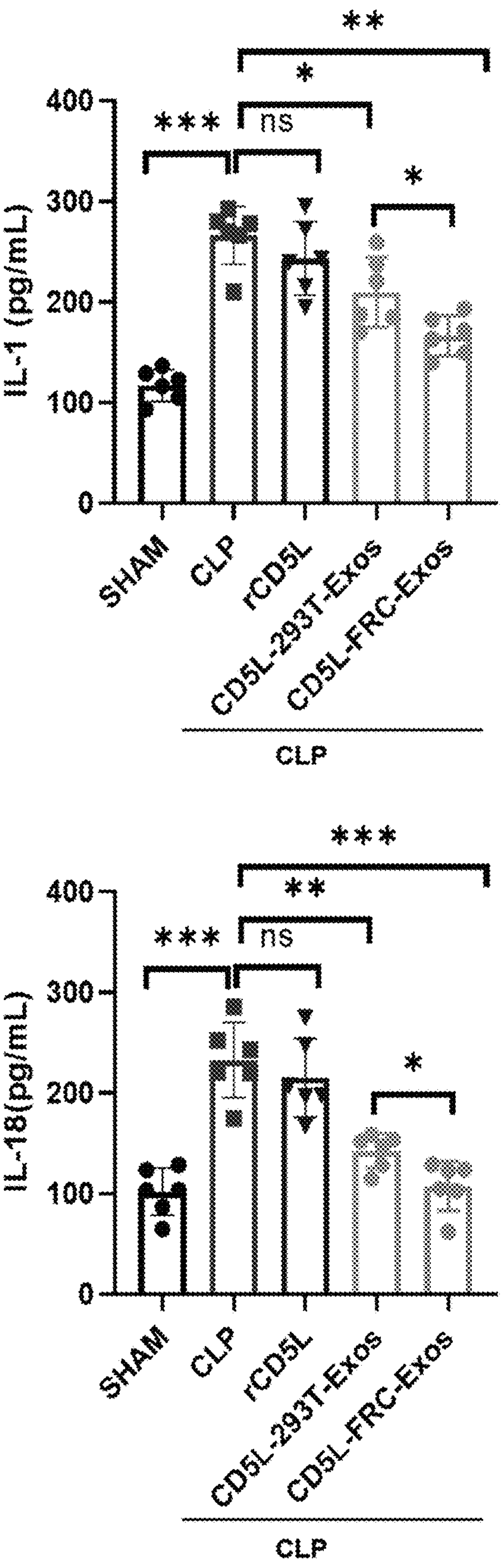

FIG. 6H: ELISA kit was used to detect IL-1 and IL-18 levels in mouse kidney tissue.

DESCRIPTION OF THE EMBODIMENTS

The following text will elaborate on the specific implementation methods and examples to further clarify the present invention and its advantages. It is important for those skilled in the art to understand that these specific implementation methods and examples are provided for illustrative purposes and not intended to limit the present invention.

Throughout the entire specification, unless otherwise specified, the terms used should be understood in their usual meanings as commonly used in the field. Therefore, unless otherwise defined, all technical and scientific terms used in this document have the same meaning as generally understood by those skilled in the art of the field to which the invention belongs. In case of any discrepancy, this specification shall take precedence.

Unless otherwise specified, various raw materials, reagents, instruments, and equipment used in the present invention can be purchased from the market or obtained through existing methods.

The technical solution of this implementation example aims to address the aforementioned technical issues. The overall approach is as follows:

This application proposes further improvements to the patent CN202111236011.6, focusing on the application of engineered extracellular vesicles in the treatment of septic acute kidney injury. However, the following technical challenges still exist:

(1) How can we ensure the effective targeting of extracellular vesicles to the kidneys?

(2) How can we achieve stable distribution within the body?

(3) How can the engineering of extracellular vesicles ensure stable and consistent drug loading efficacy?

(4) Are there long-term safety concerns and potential adverse reactions associated with the use of extracellular vesicle therapy?

As an exemplary embodiment of this invention, a novel modified extracellular vesicle that specifically targets the kidney is provided. This specific targeting modified extracellular vesicle is obtained by combining the extracellular vesicles secreted by reticular fibroblasts from the mesentery with anchor peptides that express anti-inflammatory proteins.

By combining the extracellular vesicles secreted by reticular fibroblasts from the mesentery with anchor peptides, this invention ensures the efficient targeting of the extracellular vesicles to the kidney. Furthermore, through genetic engineering of the reticular fibroblasts, the secreted extracellular vesicles can carry target molecules, specifically anti-inflammatory proteins, allowing for precise targeted therapy of the kidney. This innovative treatment strategy holds great potential for providing new possibilities in the treatment of septic acute kidney injury, positively impacting the health of patients.

By combining the extracellular vesicles secreted by reticular fibroblasts with anchor peptides, the effective targeting of extracellular vesicles to the kidney is achieved, thereby addressing the aforementioned technical challenges (1).

By controlling particle size, exosomes from fibroblasts can be regulated to have a diameter of approximately 110 nanometers, while the pore size of glomerular filtration in the kidney is typically smaller than 70 nanometers. Therefore, it can effectively ensure their stable and targeted distribution in the kidney, addressing the aforementioned technical challenge (2).

Through genetic engineering, exosomes can be modified to be enriched with specific drugs or the anti-inflammatory protein CD5L (which has been shown to have better therapeutic effects compared to other anti-inflammatory proteins). This modification enhances their drug-loading capacity. Additionally, by bypassing the capture of IgM in circulation, the half-life of exosomes carrying drugs can be extended, ensuring their sustained and consistent release of drugs within the body, thus improving the effectiveness of treatment and addressing the aforementioned technical challenge (3).

Confirmed by the article (AIM associated with the IgM pentamer: attackers on stand-by at aircraft carrier, Cell Mol Immunol. 2018 June; 15(6): 563-574.), most of the AIM (apoptosis inhibitor of macrophage) binding with IgM pentamer exhibits all of its effects in the absence of IgM. When associated with IgM pentamer, AIM is protected from renal excretion, thereby making it stable and prolonging the half-life of exosomes carrying drugs.

The modified extracellular vesicles that specifically target the kidney have been evaluated through animal experiments with long-term safety, and there are no potential adverse reactions. This addresses the technical challenge (4) mentioned above.

Subsequently, this application will be detailed in conjunction with examples and experimental data, the application of fibroblastic reticular cells derived from mesentery tissue or extracellular vesicles derived from these cells in the preparation of drugs for the treatment and/or prevention of septic acute kidney injury.

Subsequently, this application will be detailed the use of fibroblastic reticulocytes derived from mesenteric tissues or extracellular vesicles derived from these cells in the preparation of drugs for the treatment and/or prevention of septic acute kidney injury, taking into account examples and experimental data. The relevant terms of the present invention are explained as follows:

FRCs: Fibroblastic reticular cells.

FRC-Exos: Extracellular vesicles derived from fibroblastic reticular cells.

Anti-inflammatory protein-FRC-Exos: Modified extracellular vesicles loaded with anti-inflammatory proteins.

Anti-inflammatory protein-LTH-FRC-Exos: Modified extracellular vesicles specifically targeted to the kidney.

Example 1: Modified Extracellular Vesicles that Specifically Target the Kidney and Methods of Preparation Thereof First, obtaining extracellular vesicles secreted by fibroblast reticular cells (FRC-Exos) from mesenteric tissue.

1. Isolation of Fibroblastic Reticular Cells (FRCs) Derived Extracellular Vesicles (FRC-Exos) from Mesenteric Tissue:

(1) Extraction of fibroblastic reticular cells (FRCs) derived from mesenteric tissue.

(2) Cultivation of FRCs in FRCs culture medium to generate FRC-derived extracellular vesicles (Exos).

(3) Extraction of FRC-Exos from the culture medium of FRCs using ultracentrifugation.

(4) Morphological confirmation of FRC-Exos using transmission electron microscopy, revealing their prototypical, sac-like structures.

(5) Determination of the average particle size of FRC-Exos to be approximately 110 nM using nanoparticle tracking analysis (NTA).

(6) Identification of four membrane protein positive markers on FRC-Exos, including HSP70, CD81, CD63, and CD9, with negative markers being GM130, Calexin, VDAC1, and TIMM23.

(7) Utilize the Exoview imaging platform to further characterize FRC-Exos and determine the distribution of CD81 and CD9 on the surface of Exos (as illustrated in FIGS. 1A-1F).

2. Assessing the Therapeutic Effects of Extracellular Vesicles Secreted by Fibroblastic Reticular Cells (FRC-Exos) Derived from Mesenteric Tissue:

(1) Improving Survival Rate and Renal Function in Septic Mice

By injecting FRC-Exos, extracted from FRCs cultured in vitro, into septic mice, significant therapeutic effects were observed. The results demonstrate that administration of FRCs and FRC-Exos leads to notable improvements in renal function, including reductions in blood creatinine and blood urea nitrogen levels, as well as decreases in lactate dehydrogenase and acetaldehyde levels, and a decrease in pro-inflammatory cytokine levels. Furthermore, FRC-Exos promote proliferation of renal cells, reduce the number of apoptotic cells in renal tissue, and ameliorate the histopathological damage in the kidneys (FIGS. 2A-2E). These findings suggest that FRC-Exos released by FRCs alleviate renal injury caused by sepsis, enhance survival rate and renal function in mice, thus providing a potential novel approach for the treatment of septic acute kidney injury.

(2) Locating and Absorbing FRC-Exos

To investigate the uptake of FRC-Exos by renal tubular cells, we employed the use of fluorescent dye DiD to label FRC-Exos and administered them via the tail vein immediately after CLP surgery in mice. Whole kidney fluorescence was observed through in vivo imaging, revealing the presence of fluorescence in renal tissue within 24 hours post-FRC-Exos injection (FIG. 3A). Flow cytometry analysis demonstrated a significant enhancement of DiD fluorescence in renal cell suspensions following FRC-Exos injection (FIG. 3B).

Furthermore, we isolated PRTCs from mouse kidneys and added DiD or DiO-labeled FRC-Exos to the culture medium of these cells, with fluorescently labeled FRCs serving as a control in co-culture (FIG. 3C). After 24 hours of co-culture with FRCs, only a few PRTCs displayed fluorescence, while a greater number of PRTCs in the FRC-Exos group exhibited fluorescence. These findings suggest that FRC-Exos derived from FRCs can target damaged kidneys. Thus, in vitro and in vivo experiments confirm the targeting of injured kidneys by FRC-derived Exos, which are subsequently taken up by renal tubular cells.

(3) Promote Mitophagy and Inhibit Pyroptosis

FRC-Exos play a protective role in sepsis-associated acute kidney injury (S-AKI) by regulating mitophagy and pyroptosis in proximal renal tubular epithelial cells (PRTCs) (FIGS. 4A-4J):

① Transcriptome analysis revealed altered gene expression in immune system, signal transduction and metabolism pathways, suggesting a change in cellular state in LPS-treated PRTCs.

② Mitophagy regulation: Injection of FRC-Exos into septic mice led to a significant increase in autophagosomes in kidney tubular cells as observed by electron microscopy, indicating that FRC-Exos could promote mitophagy, helping to eliminate damaged mitochondria. In addition, the increased co-localization of LC3B and PINK1 indicated activation of mitophagy.

③ Pyroptosis inhibition: LPS stimulation in septic mice induced the formation of NLRP3 inflammasomes and activation of N-GSDMD, leading to pyroptosis. However, FRC-Exos injection inhibited the expression of NLRP3 inflammasomes and N-GSDMD, reducing the occurrence of pyroptosis.

④ Antioxidant effect: FRC-Exos also exhibited a potent antioxidant effect, reducing reactive oxygen species (ROS) production in septic mice kidney tissue, further diminishing the activation of NLRP3 inflammasomes. This subsequently led to reduced levels of cytokines IL-1 and IL-18, helping to maintain mitochondrial function.

In summary, FRC-Exos protect the health and function of renal tubular epithelial cells by preventing inflammation and cell death in S-AKI through these mechanisms. This mechanism may provide a new therapeutic strategy for the treatment of S-AKI.

Second, genetic engineering was performed on fibroblastic reticular cells (FRCs) to obtain extracellular vesicles (Exos) modified with anti-inflammatory protein CD5L.

1. Acquisition of the Anti-Inflammatory Protein Gene:

Mass spectrometry analysis revealed a series of proteins present in FRC-Exos, and KEGG analysis showed that these differentially expressed proteins were involved in key pathways such as infection, metabolism, atherosclerosis, and autophagy. Among these differentially expressed proteins, CD5L showed the most significant difference in expression (FIGS. 5A-5F). This suggests that CD5L may play an important role in the anti-inflammatory effects of FRC-Exos.

Subsequently, PRTCs stimulated with LPS were treated with M1-Exos or FRC-Exos for 24 hours. We found that compared to M1-Exos, FRC-Exos could activate the PINK-PARKIN pathway and reduce the formation of NLRP3 inflammasomes (FIGS. 5A-5F).

2. Selection of Stable Cell Lines:

(1) Construction of lentiviral vector pLenti-CD5L containing the coding sequence of CD5L: The CD5L gene was inserted into the BamHI and NotI restriction sites of the PG-P1-VSVG plasmid (plasmid map shown in FIGS. 5A-5F), using PCR and enzyme ligation. The primer sequences for CD5L are listed in Table 1.

TABLE 1

| Primers | Sequence (5'-3') |
|---|---|
| CD5L-F | TCAGTAGAGAGTGTCGGATCCTCACACATCAAAGTCTGTG CAGATCA (SEQ ID NO. 1) |
| CD5L-R | GGTTCCAAGCTTAAGCGGCCGCGCCACCATGGCTCCATTG TTCAACTT (SEQ ID NO. 2) |

(2) Construction of FRCs Cell Line Overexpressing CD5L: pLenti-CD5L plasmid was co-transfected with lentivirus packaging plasmids pMD2.G (Addgene #12259) and psPAX2 (Addgene #12260) into 293T cells at a ratio of 4:1:3. The transfection was carried out following the instructions of a virus packaging kit, and the virus supernatant was collected 48 hours after transfection. After centrifugation at 1500 g for 10 minutes and filtration through a 0.45 g M membrane, the supernatant was stored at −80 °C. The successfully packaged lentivirus was used to infect fibroblastic reticular cells (FRCs) with appropriate antibiotics, such as puromycin, to screen and select stable cell lines that express CD5L. Only those cell lines that successfully express and integrate the CD5L gene would survive. Finally, the CD5L overexpressing FRCs cell line was obtained via screening. In addition, empty lentivirus vector was added to control cells.

(3) The CD5L overexpressing FRCs cell line was separated by centrifugation to obtain extracellular vesicles loaded with anti-inflammatory protein modification.

Third, obtaining modified extracellular vesicles (Anti-inflammatory Protein-LTH-FRC-Exos) that specifically target the kidney 1. Obtaining KIM-1 Targeting Peptide To enhance the targeting specificity of extracellular vesicles, surface modification of the vesicles is achieved based on the principles of similarity and solubility. This involves incorporating PEG-cholesterol conjugates containing the LTH targeting peptide into the vesicles. Cholesterol is an amphiphilic molecule with both hydrophobic and hydrophilic moieties, with a stronger affinity for lipids than water. When interacting with phospholipids, cholesterol can insert itself between the phospholipid molecules, allowing the desired molecules to be connected to the vesicle's surface. Through phage display screening technology, a targeting peptide (LTH) for kidney injury molecule-1 (KIM-1) was obtained. The amino acid sequence of the KIM-1 targeting peptide is leucine-threonine-histidine-valine-valine-tryptophan-leucine.

2. Co-incubating the obtained anti-inflammatory protein-loaded modified extracellular vesicles with KIM-1 targeting peptide to obtain modified extracellular vesicles specifically targeting the kidney, referred to as anti-inflammatory protein-LTH-FRC-Exos. The specific steps are as follows:

Take 500 μg of anti-inflammatory protein-FRC-Exos and add it to a 1001 solution of KIM-1 lipopeptide targeting peptide in Buffer A at a ratio of 1:10. Incubate at room temperature with shaking at 250 rpm for 3 hours. Then, let the sample sit at 4 °C for 24 hours. Add Buffer B to bring the sample volume to 4 ml. Transfer the sample to a 100 kDa ultrafiltration tube (Millipore, UFC8100) and centrifuge at room temperature at 4000 g for 20-30 minutes until the volume is approximately 250 μl. Repeat this step twice and finally concentrate the sample volume to approximately 250 μl. After gently blowing on the membrane of the ultrafiltration tube to disrupt any remaining extracellular vesicles, transfer the sample to an empty EP tube to obtain the anti-inflammatory protein-FRC-Exos.

Through this invention, we provide an effective method for treating septic kidney injury, which can improve kidney function, reduce inflammatory response, promote mitochondrial autophagy, and improve the survival rate of sepsis. This method holds significant clinical potential in the treatment of acute kidney injury in sepsis.

Fourth, characterization of modified extracellular vesicles (anti-inflammatory protein-LTH-FRC-Exos) that specifically target the kidney.

1. Validation of Anti-Inflammatory Protein CD5L Expression:

Immunofluorescent staining with anti-CD5L antibodies was performed to confirm the successful expression of CD5L protein in FRC cells. FRC cells that expressed CD5L showed a noticeable enhancement of fluorescent signal for CD5L (FIGS. 5A-5F).

Western blot analysis was conducted using CD5L-specific antibodies to analyze the protein extracted from FRC cells. Total protein concentration was determined by BCA assay, and the Western blot results indicated an increased expression level of CD5L protein in FRC cells, as shown in the figure. This confirms the successful expression of the anti-inflammatory protein CD5L (FIGS. 5A-5F).

2. Verification of Target Specificity Using KIM-1 Lipid Anchor Labeling.

To validate the targeting specificity of KIM-1 peptide, we administered FRC-Exos, labeled with DiD and conjugated with KIM-1 peptide, to mice via intravenous injection. Comparative observations were made with the control group treated with FRC-Exos lacking KIM-1 peptide (FIGS. 5A-5F):

In vivo imaging: The targeting specificity of anti-inflammatory protein-FRC-Exos was assessed using live imaging techniques. After intravenous administration of anti-inflammatory protein-FRC-Exos, the localization and distribution of the exosomes within the kidneys were detected using fluorescence or other labeling techniques. Successful targeting specificity would be evidenced by a significant enhancement of fluorescence signals in the renal region.

Immunofluorescence: Immunofluorescent staining was performed on mouse kidney tissues. Results demonstrated that the intensity of red fluorescence was higher in the renal tissues, indicating successful targeting specificity would manifest as a pronounced increase in exosome fluorescence, specifically in the renal tubular area associated with KIM-1 fluorescence signals, compared to other areas.

Example 2. The Application of Modified Extracellular Vesicles that Specifically Target the Kidney in the Preparation of Drugs for the Treatment and/or Prevention of Sepsis-Associated Acute Kidney Injury 1. Cecal Ligation and Puncture (CLP) Induced Sepsis AKI Model Induce a septic acute kidney injury model through cecal ligation and puncture (CLP) as follows: Select male C57BL/6 mice, aged 8-12 weeks. After anesthesia, position the mice in a prone position, open the abdominal cavity, ligate the cecum at ¼ of its length, create two punctures using a 22G needle at the cecal region, expel the feces, close the abdominal cavity layer by layer, and administer subcutaneous injection of 20 ml/kg of normal saline for fluid resuscitation. (For detailed methodology, refer to Peng Z Y, et al. Crit Care Med. 2012 February; 40(2): 538-43).

2. The Mortality Rate, Renal Function Parameters, Oxidative Stress Levels, and Inflammasome Activation in Septic Mice were Monitored.

FRCs were infected with lentivirus carrying CD5L in vitro. Following viral infection, the expression of CD5L significantly increased in both FRCs and 293T cells.

FRCs and 293T cells were infected with lentivirus carrying CD5L, and the extracted Exos were co-incubated with LTH peptide. The resulting Exos were subsequently referred to as CD5L-FRC-Exos and CD5L-293T-Exos. Afterwards, mice were intravenously injected with rCD5L, CD5L-FRC-Exos, and CD5L-293T-Exos via the tail vein. The CD5L-FRC-Exos group exhibited the highest levels of CD5L and PINK1 proteins in renal tissue, and the lowest levels of N-GSDMD protein (FIG. 6B). It is worth noting that, compared to treatment with rCD5L or CD5L-293T-Exos, FRC-CD5L-Exos treatment significantly reduced the mortality rate of septic mice (FIGS. 6A-6H).

The CD5L-FRC-Exos injection has contributed to alleviating structural alterations in renal tubular epithelial cells, such as vacuolization, dilation, and loss of microvilli. Additionally, the CD5L-FRC-Exos group exhibited significantly decreased levels of Scr and BUN compared to the CLP group. Moreover, levels of MDA and LDH were also significantly reduced in the CD5L-FRC-Exos group (FIGS. 6A-6H).

Immunofluorescence results demonstrated an increase in PINK1 content in renal tissues following CD5L-FRC-Exo injection. Furthermore, the CD5L-FRC-Exos group displayed the lowest levels of IL1 and IL18 (FIGS. 6A-6H). In conclusion, these findings support the notion that modified FRC-Exos can specifically target the kidneys in sepsis, deliver CD5L substances to damaged renal tubular cells, promoting mitochondrial autophagy, ultimately improving renal function and reducing mortality.

3. The Expression of CD5L in Patients with Sepsis.

Research indicates that the expression of CD5L is significantly increased inpatients with sepsis. This finding suggests that CD5L may be associated with the onset and progression of sepsis. The dynamic expression of CD5L: The expression of CD5L appears to increase with the progression of sepsis, with the highest expression levels observed in the early stages of sepsis. This may indicate an early important role of CD5L in the pathogenesis of sepsis. Therefore, compared to other anti-inflammatory proteins secreted by reticular fibroblasts, the treatment effect is much better when extracellular vesicles secreted by reticular fibroblasts express CD5L and anchor peptides.

We further measured the levels of CD5L in the serum and urine of healthy individuals and patients with sepsis, and found a significant increase in CD5L expression in patients with sepsis (FIGS. 6A-6H). Other clinical characteristics of the patients are shown in Supplementary Table 1. We found that the levels of CD5L were highest in the early stages of sepsis diagnosis and remained elevated throughout the course of sepsis (FIGS. 6A-6H). Additionally, we observed a positive correlation between the levels of CD5L in the serum obtained 6 hours after sepsis diagnosis and the concurrently measured creatinine levels.

Through the above case studies, the present invention provides a method and composition for improving septic kidney injury, which can be used to treat patients with sepsis using FRC-Exos, improve kidney function, reduce mortality rate, and enhance the effectiveness of targeted therapy.

Lastly, it should be noted that the terms “including,” “comprising,” or any variations thereof are intended to encompass non-exclusive inclusions, thereby including not only the listed elements, but also other elements not explicitly mentioned, or inherent to the process, method, article, or device.

Although the preferred embodiments of the present invention have been described, it should be understood that those skilled in the art may make additional changes and modifications to these embodiments once they grasp the fundamental creative concept. Therefore, the appended claims are intended to cover not only the preferred embodiments, but also all variations and modifications falling within the scope of the present invention.

Clearly, those skilled in the art can make various alterations and variations to the present invention without departing from its spirit and scope. Thus, if these modifications and variations of the present invention are within the scope of the claims and the equivalent technical aspects, the present invention is also intended to include these alterations and variations.

What is claimed is:

1. A preparation method for a modified extracellular vesicle that specifically target kidneys, wherein the method includes:

expressing an anti-inflammatory protein in fibroblastic reticular cells (FRC) to obtain anti-inflammatory protein-modified extracellular vesicles;

co-incubating the anti-inflammatory protein-modified extracellular vesicles with the anchoring peptides to obtain the modified extracellular vesicles that specifically target the kidneys, which is abbreviated as anti-inflammatory protein-LTH-FRC-Exos, wherein a method of expressing the anti-inflammatory protein in FRC to obtain the anti-inflammatory protein-modified extracellular vesicles comprises:

using CD5L gene shown in SEQ ID NO. 3 as a template, obtaining a gene fragment by PCR with primers shown in SEQ ID NO. 1-SEQ ID NO. 2, and inserting the gene fragment into BamHI and NotI restriction sites of PG-P1-VSVG plasmid by using enzyme cutting and ligation to obtain lentiviral plasmid pLenti-CD5L;

co-transfecting the lentiviral plasmid pLenti-CD5L with a packaging plasmid into 293T cells to obtain successfully packaged lentivirus, and then infecting reticular fibroblasts with the lentivirus to obtain an FRC cell line overexpressing CD5L through screening;

separating and centrifuging the FRC cell line overexpressing CD5L to obtain the anti-inflammatory protein-modified extracellular vesicles.

* * * * *

SEQUENCE LISTING

```
Sequence total quantity: 3
SEQ ID NO: 1            moltype = DNA  length = 47
FEATURE                 Location/Qualifiers
source                  1..47
                        mol_type = other DNA
                        note = Artificial Sequence
                        organism = unidentified
SEQUENCE: 1
tcagtagaga gtgtcggatc ctcacacatc aaagtctgtg cagatca               47

SEQ ID NO: 2            moltype = DNA  length = 48
FEATURE                 Location/Qualifiers
source                  1..48
                        mol_type = other DNA
                        note = Artificial Sequence
                        organism = unidentified
SEQUENCE: 2
ggttccaagc ttaagcggcc gcgccaccat ggctccattg ttcaactt              48

SEQ ID NO: 3            moltype = DNA  length = 1059
FEATURE                 Location/Qualifiers
source                  1..1059
                        mol_type = other DNA
                        note = Artificial Sequence
                        organism = unidentified
SEQUENCE: 3
atggctccat tgttcaactt gatgctggcc atcttgagca tttttgttgg atcgtgtttt  60
tcagagtctc caaccaaagt gcagctagtg ggaggtgccc accgctgtga agggcgagtg  120
gaggtggaac acaatggcca gtgggggact gtgtgtgatg atggctggga ccggcgtgat  180
gtggctgtgg tgtgccgaga gctcaattgt ggagcagtca tccaaacccc gcgtggcgca  240
tcatatcagc caccagcatc agagcaaaga gttcttattc aaggggttga ctgcaacgga  300
acggaagaca cgttggctca atgtgagcta aattacgatg tttttgactg ctcacatgaa  360
gaagatgctg gggcacagtg tgagaaccca gacagtgacc tcctcttcat tccagaggat  420
gtgcgtctag tagatggccc ggggcactgc cagggtcgag tggaggtgct ccaccagtcc  480
cagtggagca ctgtgtgtaa agcaggctgg aacttacagg tctcaaaggt ggtgtgcagg  540
cagctcgggt gtgggcgggc attactgacc tacggaagct gcaacaagaa tactcagggc  600
aaaggaccca tctggatggg caagatgtcg tgttctggac aagaagcaaa ccttcggtct  660
tgccttttga gtcgtttgga gaacaactgt acccatggcg aggacacatg gatggaatgt  720
gaagatcctt ttgagctgaa gctggtggga ggagacaccc cctgctctgg gaggttggag  780
gtgctacaca agggttcctg ggctctgtc tgtgatgaca actggggaga aaaggaggac  840
caagtggtct gcaagcaact gggttgtggg aagtccctcc atccatcccc caaaacccgg  900
aaaatctatg ggcctggggc aggccgcatc tggctggatg acgtcaactg ctcagggaag  960
gaacagtctc tggagttctg ccggcacagg ttgtgggggt accacgactg tacccacaag  1020
gaagatgtgg aggtgatctg cacagacttt gatgtgtga                        1059
```